(12) United States Patent
Iaccino et al.

(10) Patent No.: US 7,977,519 B2
(45) Date of Patent: *Jul. 12, 2011

(54) PRODUCTION OF AROMATIC HYDROCARBONS FROM METHANE

(75) Inventors: Larry L. Iaccino, Seabrook, TX (US); Neeraj Sangar, League City, TX (US); Elizabeth L. Stavens, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/701,841

(22) Filed: Feb. 8, 2010

(65) Prior Publication Data
US 2011/0040135 A1    Feb. 17, 2011

Related U.S. Application Data

(63) Continuation of application No. 11/408,861, filed on Apr. 21, 2006, now Pat. No. 7,683,227.

(51) Int. Cl.
*C07C 4/22* (2006.01)

(52) U.S. Cl. ........ 585/407; 585/418; 585/419; 585/420; 585/943

(58) Field of Classification Search .................. 585/407, 585/418, 419, 420, 943
See application file for complete search history.

(56) References Cited

U.S. PATENT DOCUMENTS

| | | | |
|---|---|---|---|
| 1,922,918 A | 8/1933 | Winkler et al. | |
| 2,909,392 A | 10/1959 | Rees et al. | |
| 2,977,154 A | 3/1961 | Bourguet et al. | |
| 4,455,394 A | 6/1984 | Pinto | |
| 4,499,327 A | 2/1985 | Kaiser | |
| 4,565,803 A | 1/1986 | Schoenthal et al. | |
| 4,666,945 A | 5/1987 | Osugi et al. | |
| 4,678,861 A | 7/1987 | Mitsui et al. | |
| 4,727,206 A | 2/1988 | Clayson et al. | |
| 4,734,536 A | 3/1988 | Nagahara et al. | |
| 4,795,847 A | 1/1989 | Weitkamp et al. | |
| 5,001,295 A | 3/1991 | Angevine et al. | |
| 5,026,937 A | 6/1991 | Bricker | |
| 5,045,520 A | 9/1991 | Curry-Hyde et al. | |
| 5,254,520 A | 10/1993 | Sofianos | |
| 5,336,825 A | 8/1994 | Choudhary et al. | |
| 5,348,982 A | 9/1994 | Herbolzheimer et al. | |
| 5,385,949 A | 1/1995 | Tierney et al. | |
| 5,430,210 A | 7/1995 | Grasselli et al. | |
| 5,457,251 A | 10/1995 | Yamashita et al. | |
| 5,527,979 A | 6/1996 | Agaskar et al. | |
| 5,545,674 A | 8/1996 | Behrmann et al. | |
| 5,610,202 A | 3/1997 | Marchionna et al. | |
| 5,656,761 A | 8/1997 | Nagahara et al. | |
| 5,767,039 A | 6/1998 | Yamagishi et al. | |
| 5,969,202 A | 10/1999 | Ashida et al. | |
| 5,973,218 A | 10/1999 | Ashida et al. | |
| 6,054,497 A | 4/2000 | Sofianos et al. | |
| 6,114,279 A | 9/2000 | Fukui et al. | |
| 6,239,057 B1 | 5/2001 | Ichikawa et al. | |
| 6,504,272 B2 | 1/2003 | Sakamoto | |
| 7,589,246 B2 | 9/2009 | Iaccino et al. | |
| 2003/0144565 A1 | 7/2003 | Allison et al. | |
| 2004/0152586 A1 | 8/2004 | Ou et al. | |
| 2007/0249740 A1 | 10/2007 | Iaccino et al. | |
| 2008/0019846 A1 | 1/2008 | White et al. | |

FOREIGN PATENT DOCUMENTS

| RU | 2 135 441 | 8/1999 |
|---|---|---|
| WO | WO 03/000826 | 1/2003 |

OTHER PUBLICATIONS

Walas, S.M., "Chemical Process Equipment," Chapter 6, pp. 91-127, 1990.
Kunii, D. et al, Fluidization Engineering, Chapter 3, pp. 61-94, 1991.
Erena, J., "Study of Physical Mixtures of Cr2O3-ZnO and ZSM-5 Catalysts for the Transformation of Syngas into Liquid Hydrocarbons," Ind. Eng. Chem. Res., pp. 1211-1219, 1998.
Japan Chemical Week Incorporating Asia Report, "Benzene Synthesized Directly from Methane: Mitsubishi Chem," The Chemical Daily Co., Ltd., vol. 46, No. 2337, ISSN 0047-1755, Oct. 6, 2005.

*Primary Examiner* — Thuan Dinh Dang
(74) *Attorney, Agent, or Firm* — Andrew B. Griffis

(57) ABSTRACT

In a process for converting methane to higher hydrocarbons including aromatic hydrocarbons, a feed containing methane is contacted with a dehydrocyclization catalyst in a reaction zone under conditions effective to convert said methane to aromatic hydrocarbons. A first portion of the catalyst is transferred from the reaction zone to a heating zone, where the first catalyst portion is heated by contacting the catalyst with hot combustion gases generated by burning a supplemental source of fuel. The heated first catalyst portion is then returned to the reaction zone.

12 Claims, 6 Drawing Sheets

PRODUCTION OF AROMATIC HYDROCARBONS FROM METHANE

CROSS REFERENCE TO RELATED APPLICATIONS

This application is a Continuation Application of U.S. application Ser. No. 11/408,861, filed Apr. 21, 2006, now U.S. Pat. No. 7,683,227, which claims the benefit of priority to PCT Application No. PCT/US2005/044042, filed Dec. 2, 2005, which in turn claims benefit of priority to U.S. Provisional Application No. 60/638,922, filed on Dec. 22, 2004, each of said applications incorporated herein in their entirety.

FIELD

This invention relates to a process for producing aromatic hydrocarbons from methane and, in particular, from natural gas.

BACKGROUND

Aromatic hydrocarbons, particularly benzene, toluene, ethylbenzene and xylenes, are important commodity chemicals in the petrochemical industry. Currently, aromatics are mostly frequently produced from petroleum-based feedstocks by a variety of processes, including catalytic reforming and catalytic cracking. However, as the world supplies of petroleum feedstocks decrease, there is a growing need to find alternative sources of aromatic hydrocarbons.

One possible alternative source of aromatic hydrocarbons is methane, which is the major constituent of natural gas and biogas. World reserves of natural gas are constantly being upgraded and more natural gas is currently being discovered than oil. Because of the problems associated with transportation of large volumes of natural gas, most of the natural gas produced along with oil, particularly at remote places, is flared and wasted. Hence the conversion of alkanes contained in natural gas directly to higher hydrocarbons, such as aromatics, is a particularly attractive method of upgrading natural gas, providing the attendant technical difficulties can be overcome.

A large majority of the processes for converting methane to liquid hydrocarbons involve first conversion of the methane to synthesis gas, a blend of $H_2$ and CO. Production of synthesis gas is capital and energy intensive; therefore routes that do not require synthesis gas generation are preferred.

A number of alternative processes have been proposed for directly converting methane to higher hydrocarbons. One such process involves catalytic oxidative coupling of methane to olefins followed by the catalytic conversion of the olefins to liquid hydrocarbons, including aromatic hydrocarbons. For example, U.S. Pat. No. 5,336,825 discloses a two-step process for the oxidative conversion of methane to gasoline range hydrocarbons comprising aromatic hydrocarbons. In the first step, methane is converted to ethylene and minor amounts of $C_3$ and $C_4$ olefins in the presence of free oxygen using a rare earth metal promoted alkaline earth metal oxide catalyst at a temperature between 500° C. and 1000° C. The ethylene and higher olefins formed in the first step are then converted to gasoline range liquid hydrocarbons over an acidic solid catalyst containing a high silica pentasil zeolite.

However, these oxidative coupling methods suffer from the problems that they involve highly exothermic and potentially hazardous methane combustion reactions and that they generate large quantities of environmentally sensitive carbon oxides.

Dehydroaromatization of methane via high-temperature reductive coupling has also been proposed as a route for upgrading methane into higher hydrocarbons, particularly ethylene, benzene and naphthalene. Thus, for example, U.S. Pat. No. 4,727,206 discloses a process for producing liquids rich in aromatic hydrocarbons by contacting methane at a temperature between 600° C. and 800° C. in the absence of oxygen with a catalyst composition comprising an aluminosilicate having a silica to alumina molar ratio of at least 5:1, said aluminosilicate being loaded with (i) gallium or a compound thereof and (ii) a metal or a compound thereof from Group VIIB of the Periodic Table.

In addition, U.S. Pat. No. 5,026,937 discloses a process for the aromatization of methane which comprises the steps of passing a feed stream, which comprises over 0.5 mole percent hydrogen and 50 mole percent methane, into a reaction zone having at least one bed of solid catalyst comprising ZSM-5 and phosphorous-containing alumina at conversion conditions which include a temperature of 550° C. to 750° C., a pressure less than 10 atmospheres absolute (1000 kPaa) and a gas hourly space velocity of 400 to 7,500 hr$^{-1}$. The product effluent is said to include methane, hydrogen, at least 3 mole % $C_2$ hydrocarbons and at least 5 mole % $C_6$-$C_8$ aromatic hydrocarbons. After condensation to remove the $C_4$+ fraction, cryogenic techniques are proposed to separate the hydrogen and light hydrocarbons (methane, ethane, ethylene, etc.) in the product effluent.

U.S. Pat. Nos. 6,239,057 and 6,426,442 disclose a process for producing higher carbon number hydrocarbons, e.g., benzene, from low carbon number hydrocarbons, such as methane, by contacting the latter with a catalyst comprising a porous support, such as ZSM-5, which has dispersed thereon rhenium and a promoter metal such as iron, cobalt, vanadium, manganese, molybdenum, tungsten or a mixture thereof. The addition of CO or $CO_2$ to the feed is said to increase the yield of benzene and the stability of the catalyst.

However, existing proposals for the dehydroaromatization of methane frequently have low selectivity to aromatics and may require co-feeding of expensive additives to improve the aromatics selectivity. Moreover, any reductive coupling process generates large quantities of hydrogen and so, for economic viability, requires a route for effective utilization of the hydrogen by-product. Since natural gas fields are frequently at remote locations, effective hydrogen utilization can present a substantial challenge.

Another problem involved in the use reductive coupling to upgrade methane to higher hydrocarbons is that significant heat must be supplied to reaction. Thus not only is the process is highly endothermic, but also the reaction is thermodynamically limited. Thus the cooling effect caused by the reaction lowers the reaction temperature sufficiently to greatly reduce the reaction rate and total thermodynamic conversion if make-up heat is not provided in some manner. Various methods have been proposed for supplying heat to the aromatization of methane, but to date none of the proposed methods have proved entirely satisfactory.

For example, one known method of providing the heat of reaction to a methane aromatization process is the use of a heat-exchange fluid flowing through the reaction zone, which provides indirect heat to the catalyst in the reaction zone. However, this method of heat exchange tends to be inefficient and causes disruption of catalyst flow in non-fixed bed reactors.

It is also known to supply heat to a reaction to a methane aromatization process by using more than one reaction zone in sequence, in combination with reheating the reactants between the reaction zones. In this interstage reheating, the reactor effluent from a first bed of catalyst is heated to the desired inlet temperature of a second, downstream bed of catalyst.

One method of interstage reheating includes the use of indirect heat exchange, in which the effluent from an upstream reaction zone is passed through a heat exchanger before being fed to a subsequent reaction zone. The high temperature fluid employed in this indirect heat exchange method may be high temperature steam, combustion gases, a high temperature process stream or any other readily available high temperature fluid. This method of interstage heating does not dilute the reactants but does impose some pressure drop in the system and can expose the reactants to undesirably high temperatures.

For example, Russian Patent No. 2,135,441 discloses a process for converting methane to heavier hydrocarbons, in which the methane is mixed with at least 5 wt % of a $C_3+$ hydrocarbon, such as benzene, and then contacted with a catalyst comprising metallic platinum having a degree of oxidation greater than zero at a methane partial pressure of at least 0.05 MPa and a temperature of at least 440° C. The process is conducted in a multi-stage reactor system using interstage reheating by indirect heat exchange. Hydrogen generated in the process may be contacted with oxides of carbon to generate additional methane that, after removal of the co-produced water, can be added to the methane feed. The products of the methane conversion are a $C_2$-$C_4$ gaseous phase and a $C_5+$ liquid phase but, according the Examples, there is little (less than 5 wt %) or no net increase in aromatic rings as compared with the feed.

Another method of interstage heating is the oxidative reheat method that involves the admixture of a controlled amount of oxygen into the reactants and the selective oxidation of hydrogen generated in the aromatization process. The oxidation is accomplished in the presence of a catalyst that selectively promotes the oxidation of hydrogen as compared to the destructive combustion or oxidation of the more valuable feed and product hydrocarbons. However, the reaction generates steam that can be detrimental to the aromatization catalyst and can react with methane to form hydrogen and carbon monoxide. Moreover, by using a second selective oxidation catalyst, this method suffers from added complexity and cost.

An alternative approach to supplying heat of reaction to the reductive coupling process makes use of the fact that the catalyst generates coke as the aromatization reaction proceeds. This coke gradually deactivates the catalyst and hence the catalyst must be repeatedly regenerated to remove the coke and reactivate the catalyst. The regeneration, which involves contacting the catalyst with an oxygen-containing gas, is highly exothermic and hence can be used as a source of sensible heat to the overall process. Such a process is disclosed in International Patent Publication No WO 03/000826, in which a dehydroaromatization catalyst is circulated between a reactor system and a regenerator system, where the catalyst is contacted with different regeneration gases, including $O_2$, $H_2$, and $H_2O$, at different times to regenerate different portions of catalyst. The percentage of catalyst contacting each regeneration gas is controlled to maintain the reactor system and regeneration system under a heat balance regime. The reactor system includes a fluidized bed of catalyst in a riser reactor, and the regeneration system includes a second fluidized bed of catalyst maintained in a bubbling bed reactor.

However, processes that use the catalyst regeneration step to supply reaction heat suffer from the problem that the catalyst needs to be heated well above the target reaction temperature in the regeneration process, which leads to accelerated catalyst degradation and hence reduced catalyst life. Moreover, to maintain heat balance, the process requires a high selectivity to coke rather than to the desired aromatic products.

There is therefore a need for an improved process for supplying heat of reaction to the aromatization of methane.

SUMMARY

In one aspect, the present invention resides in a process for converting methane to higher hydrocarbons including aromatic hydrocarbons, the process comprising:

(a) contacting a feed containing methane with a dehydrocyclization catalyst in a reaction zone under conditions effective to convert said methane to aromatic hydrocarbons;

(b) transferring a first portion of said catalyst from the reaction zone to a heating zone;

(c) heating the first catalyst portion in the heating zone by contacting the catalyst with hot combustion gases generated by burning a supplemental source of fuel; and (d) returning the heated first catalyst portion to the reaction zone.

Conveniently, said first catalyst portion is contacted directly with said source of fuel in said heating (c). Alternatively, said source of fuel is burned in a combustion zone separate from said heating zone and the combustion gases generated in the combustion zone are fed to the heating zone.

Conveniently, said supplemental source of fuel comprises a hydrocarbon and/or hydrogen.

Where the supplemental source of fuel comprises a hydrocarbon, the hydrocarbon is preferably methane and said supplemental source of fuel preferably comprises part of the feed contacted in (a). Conveniently, the hydrocarbon fuel is burned in an oxygen-lean atmosphere to produce synthesis gas and the synthesis gas is conveniently used to generate additional hydrocarbon product and/or fuel.

Where the supplemental source of fuel comprises hydrogen, said fuel comprises hydrogen generated as a by-product of said contacting (a).

Conveniently, said heating zone is elongated and heat is applied to said first catalyst portion at a plurality of locations spaced along the length of the heating zone. In one embodiment, substantially all of the supplemental fuel is supplied to one end of the heating zone and oxygen-containing gas is supplied incrementally to said heating zone at said plurality of spaced locations. In another embodiment, substantially all of the oxygen-containing gas is supplied to one end of the heating zone and the supplemental fuel is supplied incrementally to said heating zone at said plurality of spaced locations. In a further embodiment, said hot combustion gases are generated in a combustion zone separate from said heating zone and are supplied to said plurality of spaced locations.

Preferably, the process further includes transferring a second portion of the catalyst to a regeneration zone separate from said heating zone and contacting said second catalyst portion with a regeneration gas in said regeneration zone to remove at least part of the coke generated by said contacting (a).

Conveniently, the temperature of the regeneration zone is at or below the temperature of the reaction zone.

In a further aspect, the invention resides in a process for converting methane to higher hydrocarbons including aromatic hydrocarbons, the process comprising:

(a) contacting a feed containing methane with a dehydrocyclization catalyst in a reaction zone under conditions effective to convert said methane to aromatic hydrocarbons;

(b) transferring a first portion of said catalyst from the reaction zone to a heating zone;

(c) heating the first catalyst portion in the heating zone by direct contact of the catalyst with hot combustion gases generated by burning a supplemental source of fuel;

(d) returning the heated first catalyst portion to the reaction zone;

(e) transferring a second portion of said catalyst from the reaction zone to a regeneration zone separate from said heating zone;

(f) contacting said second catalyst portion with a regeneration gas in said regeneration zone under conditions effective to at least partially remove coke from said second catalyst portion; and (g) returning the regenerated second catalyst portion to the reaction zone.

Conveniently, said transferring (b) and (e) and said returning (d) and (g) are effected continuously.

Conveniently, said reaction zone comprises a vertically-disposed, settling bed reactor wherein said feed enters the reactor at or near the base of the reactor and the heated first catalyst portion and the regenerated second catalyst portion are returned to the reactor at or near the top of the reactor. Conveniently, said first and second catalyst portions are removed in (b) from at or near the base of the reactor. Conveniently, said aromatic hydrocarbons are recovered from the reactor at or near the top of the reactor.

As used herein, the term "dehydrocyclization catalyst" is intended to include not only the active component(s) of the catalyst but also any inert solids which may be present in addition to the active component(s) to enhance the physical properties of the catalyst and/or to aid heat transfer.

DETAILED DESCRIPTION OF THE EMBODIMENTS

Figure 1:
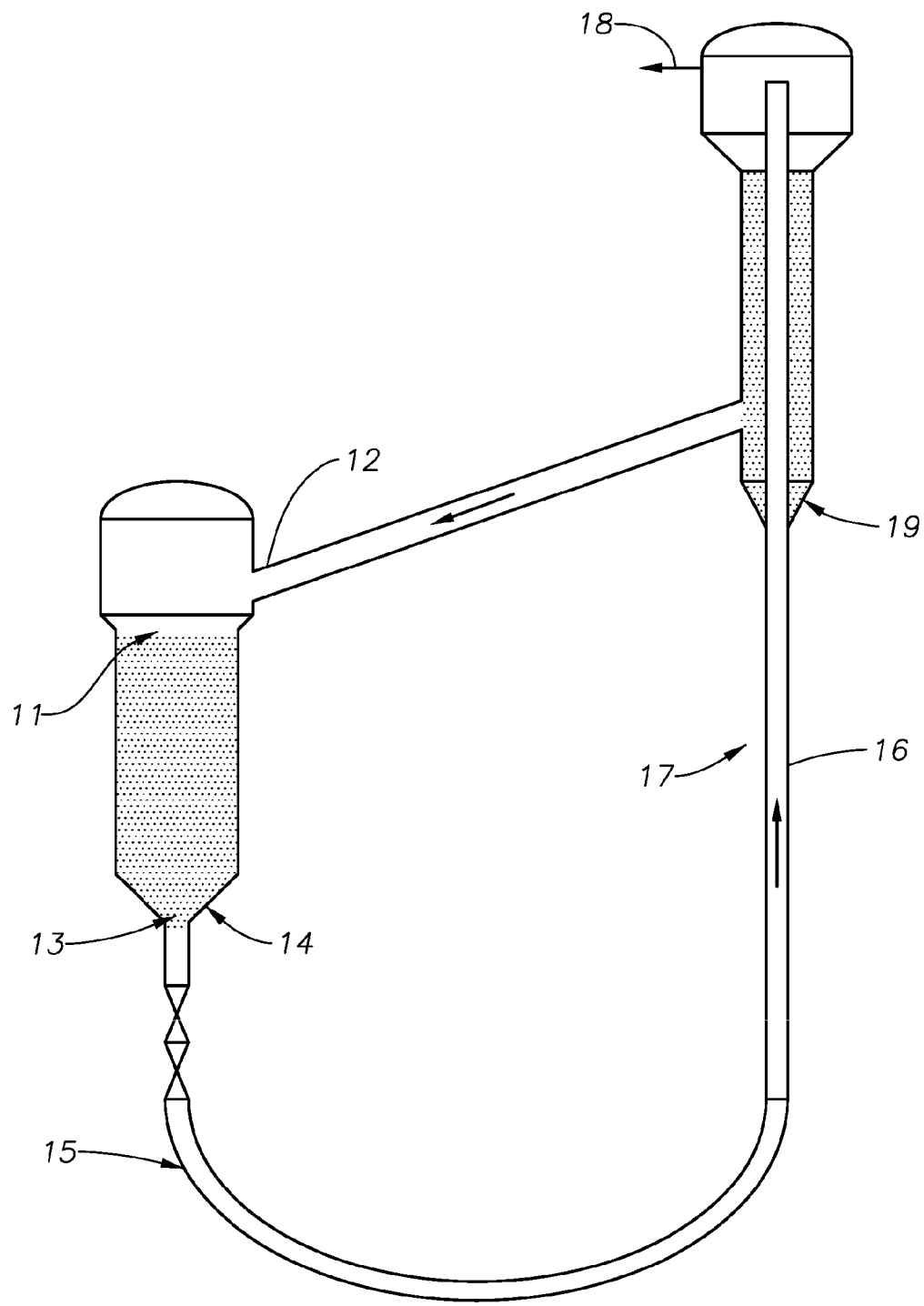
FIG. 1 is a diagram of a dehydrocyclization reactor and catalyst reheater according to a first embodiment of the invention.

As used herein the term "higher hydrocarbon(s)" means: hydrocarbon(s) having more than one carbon atom per molecule, oxygenate having at least one carbon atom per molecule, e.g., ethane, ethylene, propane, propylene, benzene, toluene, xylenes, naphthalene, and/or methyl naphthalene; and/or organic compound(s) comprising at least one carbon atom and at least one non-hydrogen atom, e.g., methanol, ethanol, methylamine, and/or ethylamine.

As used herein the term "aromatic hydrocarbon(s)" means molecules containing one or more aromatic rings. Examples of aromatic hydrocarbons are benzene, toluene, xylenes, naphthalene, and methylnaphthalenes.

As used herein the term "moving bed" reactor means a zone or vessel with contacting of solids and gas flows such that the superficial gas velocity (U) is below the velocity required for dilute-phase pneumatic conveying of solid particles in order to maintain a solids bed with void fraction below 95%. A moving-bed reactor may operate under several flow regimes including settling- or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$). These different fluidization regimes have been described in, for example, Kunii, D., Levenspiel, O., Chapter 3 of *Fluidization Engineering*, $2^{nd}$ Edition, Butterworth-Heinemann, Boston, 1991 and Walas, S. M., Chapter 6 of *Chemical Process Equipment*, Butterworth-Heinemann, Boston, 1990.

As used herein the term "settling bed" means a zone or vessel wherein particulates contact with gas flows such that the superficial gas velocity (U) is below the minimum velocity required to fluidize the solid particles, the minimum fluidization velocity ($U_{mf}$), $U<U_{mf}$, in at least a portion of the reaction zone, and/or operating at a velocity higher than the minimum fluidization velocity while maintaining a gradient in gas and/or solid property (such as, temperature, gas or solid composition, etc.) axially up the reactor bed by using reactor internals to minimize gas-solid back-mixing. Description of the minimum fluidization velocity is given in, for example Chapter 3 of "Fluidization Engineering," D. Kunii and O. Levenspiel, $2^{nd}$ Edition, Butterworth-Heinemann, Boston, 1991 and Chapter 6 of "Chemical Process Equipment," S. M. Walas, Butterworth-Heinemann, Boston, 1990, the entirety of which are incorporated by reference.

As used herein the term "fluidized bed" reactor means a zone or vessel with contacting of solids and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. As used herein the term "cascaded fluid-beds" means a series arrangement of individual fluid-beds such that there can be a gradient in gas and/or solid property (such as, temperature, gas or solid composition, pressure etc.) as the solid or gas cascades from one fluid-bed to another. Locus of minimum fluidization velocity is given in, for example, the Kunii and Walas publications noted above.

As used herein the term "riser" reactor means a zone or vessel (such as, vertical cylindrical pipe) used for net upwards transport of solids in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in the Kunii and Walas publications noted above.

The present invention provides a process for producing aromatic hydrocarbons by contacting a feedstock containing methane, typically together with $H_2$, CO and/or $CO_2$, with a dehydrocyclization catalyst in a reaction zone under conditions effective to convert the methane to aromatic hydrocarbons and hydrogen. As discussed above, the dehydrocyclization reaction is endothermic and the present invention provides a method for supplying heat to the reaction by withdrawing a portion of the catalyst from the reaction zone, heating the catalyst portion in a heating zone with hot combustion gases generated by burning a supplemental source of fuel and then returning the heated catalyst portion to the reaction zone.

In addition, the invention provides a process for utilizing the hydrogen generated as a by-product of the dehydrocyclization reaction and in particular to a process for converting at least part of the hydrogen to higher value products.

Feedstock

Any methane-containing feedstock can be used in the process of the invention but in general the present process is intended for use with a natural gas feedstock. Other suitable methane-containing feedstocks include those obtained from sources such as coal beds, landfills, agricultural or municipal waste fermentation, and/or refinery gas streams.

Methane-containing feedstocks, such as natural gas, typically contain carbon dioxide and ethane in addition to methane. Ethane and other aliphatic hydrocarbons that may be present in the feed can of course be converted to desired aromatics products in the dehydrocyclization step. In addition, as will be discussed below, carbon dioxide can also be converted to useful aromatics products either directly in the dehydrocyclization step or indirectly through conversion to methane and/or ethane in the hydrogen rejection step.

Nitrogen and/or sulfur impurities are also typically present in methane-containing streams may be removed, or reduced to low levels, prior to use of the streams in the process of the invention. In an embodiment, the feed to the dehydrocyclization step contains less than 100 ppm, for example less than 10 ppm, such as less than 1 ppm each of nitrogen and sulfur compounds.

In addition to methane, the feed to the dehydrocyclization step may contain at least one of hydrogen, water, carbon monoxide and carbon dioxide in order to assist in coke mitigation. These additives can be introduced as separate co-feeds or can be present in the methane stream, such as, for example, where the methane stream is derived from natural gas containing carbon dioxide. Other sources of carbon dioxide may include flue gases, LNG plants, hydrogen plants, ammonia plants, glycol plants and phthalic anhydride plants.

In one embodiment, the feed to the dehydrocyclization step contains carbon dioxide and comprises about 90 to about 99.9 mol %, such as about 97 to about 99 mol %, methane and about 0.1 to about 10 mol %, such as about 1 to about 3 mol %, $CO_2$. In another embodiment, the feed to the dehydrocyclization step contains carbon monoxide and comprises about 80 to about 99.9 mol %, such as about 94 to about 99 mol %, methane and about 0.1 to about 20 mol %, such as about 1 to about 6 mol %, CO. In a further embodiment, the feed to the dehydrocyclization step contains steam and comprises about 90 to about 99.9 mol %, such as about 97 to about 99 mol %, methane and about 0.1 to about 10 mol %, such as about 1 to about 5 mol %, steam. In yet a further embodiment, the feed to the dehydrocyclization step contains hydrogen and comprises about 80 to about 99.9 mol %, such as about 95 to about 99 mol %, methane and about 0.1 to about 20 mol %, such as about 1 to about 5 mol %, hydrogen.

The feed to the dehydrocyclization step can also contain higher hydrocarbons than methane, including aromatic hydrocarbons. Such higher hydrocarbons can be recycled from the hydrogen rejection step, added as separate co-feeds or can be present in the methane stream, such as, for example, when ethane is present in a natural gas feed. Higher hydrocarbons recycled from the hydrogen rejection step typically include one-ring aromatics and/or paraffins and olefins having predominately 6 or less, such as 5 or less, for example 4 or less, typically 3 or less carbon atoms. In general, the feed to the dehydrocyclization step contains less than 5 wt %, such as less than 3 wt %, of $C_3+$ hydrocarbons.

Dehydrocyclization

In the dehydrocyclization step of the present process, the methane containing feedstock is contacted with a dehydrocyclization catalyst under conditions, normally non-oxidizing conditions and preferably reducing conditions, effective to convert the methane to higher hydrocarbons, including benzene and naphthalene. The principal net reactions involved are as follows:

  (Reaction 1)

  (Reaction 2)

  (Reaction 3)

Carbon monoxide and/or dioxide that may be present in the feed improves catalyst activity and stability by facilitating reactions such as:

  (Reaction 4)

but negatively impacts equilibrium by allowing competing net reactions, such as;

  (Reaction 5).

Suitable conditions for the dehydrocyclization step include a temperature of about 400° C. to about 1200° C., such as about 500° C. to about 975° C., for example about 600° C. to about 950° C., a pressure of about 1 kPa to about 1000 kPa, such as about 10 to about 500 kPa, for example about 50 kPa to about 200 kPa and a weight hourly space velocity of about 0.01 to about 1000 $hr^{-1}$, such as about 0.1 to about 500 $hr^{-1}$, for example about 1 to about 20 $hr^{-1}$. Conveniently, the dehydrocyclization step is conducted in the absence of $O_2$.

Any dehydrocyclization catalyst effective to convert methane to aromatics can be used in the present process, although generally the catalyst will include a metal component, particularly a transition metal or compound thereof, on an inorganic support. Conveniently, the metal component is present in an amount between about 0.1% and about 20%, such as between about 1% and about 10%, by weight of the total catalyst. Generally, the metal will be present in the catalyst in the form of a carbide.

Suitable metal components for the catalyst include calcium, magnesium, barium, yttrium, lanthanum, scandium, cerium, titanium, zirconium, hafnium, vanadium, niobium, tantalum, chromium, molybdenum, tungsten, manganese, rhenium, iron, ruthenium, cobalt, rhodium, iridium, nickel, palladium, copper, silver, gold, zinc, aluminum, gallium, silicon, germanium, indium, tin, lead, bismuth and transuranium metals. Such metal components may be present in elemental form or as metal compounds, such as oxides, carbides, nitrides and/or phosphides, and may be employed alone or in combination. Platinum and osmium can also be used as one of the metal component but, in general, are not preferred.

The inorganic support may be either amorphous or crystalline and in particular may be an oxide, carbide or nitride of boron, aluminum, silicon, phosphorous, titanium, scandium, chromium, vanadium, magnesium, manganese, iron, zinc, gallium, germanium, yttrium, zirconium, niobium, molybdenum, indium, tin, barium, lanthanum, hafnium, cerium, tantalum, tungsten, or other transuranium elements. In addition, the support may be a porous material, such as a microporous crystalline material or a mesoporous material. As used herein the term "microporous" refers to pores having a diameter of less than 2 nanometers, whereas the term "mesoporous" refers to pores having a diameter of from 2 to 50 nanometers.

Suitable microporous crystalline materials include silicates, aluminosilicates, titanosilicates, aluminophosphates, metallophosphates, silicoaluminophosphates or their mixtures. Such microporous crystalline materials include materials having the framework types MFI (e.g., ZSM-5 and silicalite), MEL (e.g., ZSM-11), MTW (e.g., ZSM-12), TON (e.g., ZSM-22), MTT (e.g., ZSM-23), FER (e.g., ZSM-35), MFS (e.g., ZSM-57), MWW (e.g., MCM-22, PSH-3, SSZ-25, ERB-1, ITQ-1, ITQ-2, MCM-36, MCM-49 and MCM-56), IWR (e.g., ITQ-24), KFI (e.g., ZK-5), BEA (e.g., zeolite beta), ITH (e.g., ITQ-13), MOR (e.g., mordenite), FAU (e.g., zeolites X, Y, ultrastabilized Y and dealuminized Y), LTL (e.g., zeolite L), IWW (e.g., ITQ-22), VFI (e.g., VPI-5), AEL (e.g., SAPO-11), AFI (e.g., ALPO-5) and AFO (SAPO-41), as well as materials such as MCM-68, EMM-1, EMM-2, ITQ-23, ITQ-24, ITQ-25, ITQ-26, ETS-2, ETS-10, SAPO-17, SAPO-34 and SAPO-35. Suitable mesoporous materials include MCM-41, MCM-48, MCM-50, FSM-16 and SBA-15.

Examples of preferred catalysts include molybdenum, tungsten, rhenium and compounds and combinations thereof on ZSM-5, silica or alumina.

The metal component can be dispersed on the inorganic support by any means well known in the art such as co-precipitation, incipient wetness, evaporation, impregnation, spray-drying, sol-gel, ion-exchange, chemical vapor deposition, diffusion and physical mixing. In addition, the inorganic support can be modified by known methods, such as, for example, steaming, acid washing, caustic washing and/or treatment with silicon-containing compounds, phosphorus-containing compounds, and/or elements or compounds of Groups 1, 2, 3 and 13 of the Periodic Table of Elements. Such modifications can be used to alter the surface activity of the support and hinder or enhance access to any internal pore structure of the support.

The dehydrocyclization step is conducted by contacting the methane-containing feedstock with the dehydrocyclization catalyst in one or more fixed bed, moving bed or fluidized bed reaction zones. Generally, the feedstock is contacted in the or each reaction zone with a moving bed of dehydrocyclization catalyst, wherein the feedstock flows countercurrent to the direction of movement of the dehydrocyclization catalyst. In one embodiment, the reaction zone comprises a settling bed reactor, by which is meant a vertically disposed reactor in which particulate catalyst enters at or near the top of the reactor and flows under gravity to form a catalyst bed, while the feed enters the reactor at or near the base of the reactor and flows upwardly through the catalyst bed. In an alternative embodiment, the reaction zone comprises a plurality of series-connected fluidized bed reactors in which particulate catalyst is cascaded in one direction from one reactor to the next adjacent reactor in the series, while the feed is passed through and between the reactors in the opposite direction.

The dehydrocyclization reaction is endothermic and in order to supply heat to the reaction, a first portion of the catalyst is withdrawn from the reaction zone, either on an intermittent, or more preferably, a continuous basis, and transferred to a separate heating zone, where the first catalyst portion is heated by direct contact with hot combustion gases generated by burning a supplemental source of fuel. The heated first catalyst portion is then returned to the reaction zone.

By "supplemental source of fuel" is meant that the source fuel is physically separate from the catalyst and hence is not, for example, coke generated on the catalyst as a by-product of the dehydrocyclization reaction. Typically, the supplemental source of fuel comprises a hydrocarbon, such as methane, and in particular a suitable fuel source is the natural gas used as the feedstock to the process. Conveniently, an oxygen-lean atmosphere is maintained in the heating zone so that burning the hydrocarbon fuel to heat the first catalyst portion produces synthesis gas, which can then be used to generate additional hydrocarbon product and/or fuel. In addition, the use of an oxygen-lean atmosphere inhibits oxidation of metal carbides present in the dehydrocyclization catalyst and minimizes the average steam partial pressure thereby reducing catalyst hydrothermal aging.

Alternatively, a suitable supplemental fuel source is hydrogen and, in particular, part of the hydrogen generated as a by-product of the aromatization reaction.

Conveniently, said first catalyst portion is contacted directly with the burning source of fuel in the heating zone. Alternatively, the source of fuel is burned in a combustion zone separate from said heating zone and the combustion gases generated in the combustion zone are fed to the heating zone to heat the first catalyst portion.

In one practical embodiment, the heating zone is elongated and the first catalyst portion is passed through the heating zone from an inlet at or adjacent one end of the heating zone to an outlet at or adjacent the other end of the heating zone, with heat being applied to first catalyst portion at a plurality of locations spaced along the length of the heating zone. In this way, the heat input to the first catalyst portion can be distributed along the length of the heating zone thereby minimizing catalyst surface temperatures and internal gradients.

Where the first catalyst portion is heated by direct contact with the burning source of fuel in the heating zone, gradual heating of the catalyst can be achieved by supplying substantially all of the supplemental fuel to the inlet end of the heating zone and then supplying the oxygen-containing gas incrementally to said heating zone at said plurality of spaced locations along the length of heating zone. Alternatively, substantially all of the oxygen-containing gas required to burn said supplemental fuel can be supplied to the inlet end of the heating zone and the supplemental fuel supplied incrementally to the heating zone at said plurality of spaced locations.

Where the first catalyst portion is heated by direct contact with hot combustion gases generated in a separate combustion zone, gradual heating of the catalyst can be achieved by supplying the hot combustion gases to said plurality of spaced locations along the length of heating zone.

In one embodiment, the heating zone is a riser and said first catalyst portion is passed upwardly through the riser during the reheating step. In practice, the heating zone may include a plurality of risers connected in parallel. Alternatively, said heating zone can include a moving bed of said catalyst.

Typically, the first catalyst portion is at a temperature of about 500° C. to about 900° C. on entering the heating zone and is at a temperature of about 800° C. to about 1000° C. on leaving the heating zone. The hot combustion gases are typically at a temperature of less than 1300° C., preferably less than 1100° C., more preferably less than 1000° C., for example at a temperature in the range of about 800° C. to less than 1000° C. Typically, the heating zone will be operated at pressures between 10 and 100 psia (69 and 690 kPa), more preferably between 15 and 60 psia (103 and 414 kPa). Typically, the average residence time of catalyst particles in the heating zone will be between 0.1 and 100 seconds, more preferably between 1 and 10 seconds.

Prior to being reintroduced into the reaction zone and, preferably after passage through the heating zone, the first catalyst portion may be subjected to one or more stripping steps to at least partially remove (a) coke or heavy hydrocarbons that may have been produced on the surface of the catalyst and/or (b) water or oxygen that may have been adsorbed by the catalyst. Stripping to remove coke or heavy hydrocarbons is conveniently effected by contacting the first catalyst portion with steam, hydrogen and/or $CO_2$, whereas stripping to remove water or oxygen is conveniently effected by contacting the first catalyst portion with methane, $CO_2$ or hydrogen.

In addition, since the reheating step may tend to oxidize catalytically active metal species, particularly metal carbides, contained by the first catalyst portion, the reheated catalyst is preferably subjected to a carburizing step prior to being reintroduced into the reaction zone. Conveniently, the carburization step is effected by contacting the first catalyst portion with $H_2$, and CO, $CO_2$, and/or a hydrocarbon, such as methane, ethane, or propane, and can be conducted simultaneously with or separately from the water/oxygen stripping step.

As well as being endothermic, the dehydrocyclization reaction tends to deposit coke on the catalyst and hence, to maintain the activity of the dehydrocyclization catalyst, a second portion of the catalyst is withdrawn from the reaction zone, either on an intermittent, or more preferably, a continuous basis, and transferred to a separate regeneration zone. The gas used to transport the second catalyst portion to the regeneration zone may contain $O_2$ but preferably contains less $O_2$ than air, such as less than 10 wt % $O_2$, most preferably less than 5% $O_2$. The transporting gas may contain $CO_2$ and/or $H_2$ to gasify a portion of the coke from the second catalyst portion, but preferably is substantially free of $H_2O$ and is at a low temperature (typically less than 200° C.) so that the catalyst stream does not oxidize and heat up above the target temperature of the regeneration zone.

In the regeneration zone, the second catalyst portion is contacted with an oxygen-containing gas under conditions to at least partially remove the coke on the catalyst and thereby regenerate the catalyst. The regeneration gas preferably contains less $O_2$ than air, such as less than 10 wt %, more preferably less than 5 wt %, $O_2$, and is preferably substantially free of $H_2O$. The regeneration gas may also contain $CO_2$ to gasify a portion of the coke from the second catalyst portion. Convenient sources of the regeneration gas are an $O_2$ depleted, $N_2$ enriched stream from an air separation unit and a high $CO_2$ reject stream from industrial or natural gas processing to which air or $O_2$ has been added to achieve the target $O_2$ concentration. Typically the regeneration gas is circulated between the regeneration zone and treatment zone, where the used regeneration gas is cooled to condense out excess water, make-up oxygen-containing gas (preferably air) is added to maintain the target $O_2$ concentration and a portion is purged to maintain constant pressure. Typically the regeneration zone will be operated at pressures between 10 and 100 psia (69 and 690 kPa), more preferably between 15 and 60 psia (103 and 414 kPa).

The regeneration zone may be a reactor operated as a fluidized bed, an ebulating bed, a settling bed, a riser reactor or a combination thereof. In practice, the regeneration zone may include a plurality of reactors, such as a plurality of riser reactors connected in parallel. The regeneration zone should be operated at the minimum temperature required to remove the required amount of coke at the design residence time and in particular the temperature should not exceed the point at which metal oxide volatilization occurs or the catalyst substrate undergoes rapid deterioration. Generally, the temperature in the regeneration zone is less than the temperature of the reaction zone and typically regeneration zone temperature is from about 400° C. to about 700° C., such as from about 550° C. to about 650° C. Catalyst residence time in the regeneration zone also should be minimized to reduce catalyst aging rate and maximize percent of time the catalyst spends in the reactor doing useful work. Typically, the average residence time of catalyst particles in the regeneration zone will be between 0.1 and 100 minutes, more preferably between 1 and 20 minutes.

After leaving the regeneration zone, the second catalyst portion is returned to the reaction zone, although it may be desirable to contact the regenerated second catalyst portion with methane to at least partially remove adsorbed water and/or oxygen therefrom before the regenerated catalyst is reintroduced into the reaction zone. In addition, it may be desirable to subject the regenerated second catalyst portion to a carburization step by contacting with $H_2$, and CO, $CO_2$, and/or a hydrocarbon, such as methane, ethane, or propane, prior to reintroducing the regenerated catalyst into the reaction zone. Water/oxygen stripping and carburization of the regenerated catalyst may be effected in a single step or as separate steps.

Conveniently, the ratio of the weight of the first catalyst portion transferred in a given time to the heating zone to the weight of second catalyst portion transferred in the same time to the regeneration zone is in the range of about 5:1 to about 100:1, preferably about 10:1 to about 20:1.

In one practical embodiment, the dehydrocyclization step is conducted in a vertically-disposed, settling bed reactor with the feedstock entering the reactor at or near its base and the heated first catalyst portion and the regenerated second catalyst portion being returned to the reactor at or near the top of the reactor. Conveniently, said first and second catalyst portions are removed from at or near the base of the reactor and the process effluent is recovered from at or near the top of the reactor.

In an alternative embodiment, the dehydrocyclization step is conducted in a plurality of fluidized bed reactors connected in series, with the feedstock entering the first reactor in the series and the heated first catalyst portion and the regenerated second catalyst portion being returned to the final reactor in the series. Conveniently, said first and second catalyst portions are removed from the first reactor.

The major components of the effluent from the dehydrocyclization step are hydrogen, benzene, naphthalene, carbon monoxide, ethylene, and unreacted methane. Typically, the effluent contains at least 5 wt %, such as at least 10 wt %, for example at least 20 wt %, preferably at least 30 wt %, more aromatic rings than the feed.

The benzene and naphthalene are then recovered from the dehydrocyclization effluent, for example, by solvent extraction followed by fractionation. However, as will be discussed below, at least part of these aromatic components can be submitted to an alkylation step, before or after product recovery, to produce higher value materials, such as xylenes.

Hydrogen Management

Since hydrogen is a major component of the dehydrocyclization effluent, after recovery of the aromatic products, the effluent is subjected to a hydrogen rejection step to reduce the hydrogen content of the effluent before the unreacted methane is recycled to the dehydrocyclization step and to maximize feed utilization. Typically the hydrogen rejection step comprises reacting at least part of the hydrogen in the dehydrocyclization effluent with an oxygen-containing species, preferably CO and/or $CO_2$, to produce water and a second effluent stream having a reduced hydrogen content compared with the first (dehydrocyclization) effluent stream. Suitable hydrogen rejection processes are described below and in our copending PCT Application No. PCT/US2005/044042, filed on Dec. 2, 2005.

Conveniently, the hydrogen rejection step includes (i) methanation and/or ethanation, (ii) a Fischer-Tropsch process, (iii) synthesis of $C_1$ to $C_3$ alcohols, particularly methanol, and other oxygenates, (iv) synthesis of light olefins, paraffins and/or aromatics by way of a methanol or dimethyl ether intermediate and/or (v) selective hydrogen combustion. These steps may be employed sequentially to gain the greatest benefit; for example Fischer-Tropsch may first be employed to yield a $C_2$+ enriched stream followed by methanation to achieve high conversion of the $H_2$.

Typically, as described below, the hydrogen rejection step will generate hydrocarbons, in which case, after separation of the co-produced water, at least portion of the hydrocarbons are conveniently recycled to the dehydrocyclization step. For example, where the hydrocarbons produced in the hydrogen rejection step comprise paraffins and olefins, the portion recycled to the dehydrocyclization step conveniently comprises, paraffins or olefins with 6 or less carbon atoms, such as 5 or less carbon atoms, for example 4 or less carbon atoms or 3 or less carbon atoms. Where, the hydrocarbons produced in the hydrogen rejection step comprise aromatics, the portion recycled to the dehydrocyclization step conveniently comprises single ring aromatic species.

Methanation/Ethanation

In one embodiment the hydrogen rejection step comprises reaction of at least part of the hydrogen in the dehydrocyclization effluent with carbon dioxide to produce methane and/or ethane according to the following net reactions:

$$CO_2 + 4H_2 \leftrightarrow CH_4 + 2H_2O \quad \text{(Reaction 6)}$$

$$2CO_2 + 7H_2 \leftrightarrow C_2H_6 + 4H_2O \quad \text{(Reaction 7)}$$

The carbon dioxide employed is conveniently part of a natural gas stream and preferably the same natural gas stream used as the feed to the dehydrocyclization step. Where the carbon dioxide is part of a methane-containing stream, the $CO_2$:$CH_4$ of the stream is conveniently maintained between about 1:1 and about 0.1:1. Mixing of the carbon dioxide-containing stream and the dehydrocyclization effluent is conveniently achieved by supplying the gaseous feeds to the inlet of a jet ejector.

The hydrogen rejection step to produce methane or ethane normally employs a $H_2$:$CO_2$ molar ratio close to the stoichiometric proportions required for the desired Reaction 6 or Reaction 7, although small variations can be made in the stoichiometric ratio if it is desired to produce a $CO_2$-containing or $H_2$-containing second effluent stream. The hydrogen rejection step to produce methane or ethane is conveniently effected in the presence of a bifunctional catalyst comprising a metal component, particularly a transition metal or compound thereof, on an inorganic support. Suitable metal components comprise copper, iron, vanadium, chromium, zinc, gallium, nickel, cobalt, molybdenum, ruthenium, rhodium, palladium, silver, rhenium, tungsten, iridium, platinum, gold, gallium and combinations and compounds thereof. The inorganic support may be an amorphous material, such as silica, alumina or silica-alumina, or like those listed for the dehydroaromatization catalyst. In addition, the inorganic support may be a crystalline material, such as a microporous or mesoporous crystalline material. Suitable porous crystalline materials include the aluminosilicates, aluminophosphates and silicoaluminophosphates listed above for the dehydrocyclization catalyst.

The hydrogen rejection step to produce methane and/or ethane can be conducted over a wide range of conditions including a temperature of about 100° C. to about 900° C., such as about 150° C. to about 500° C., for example about 200° C. to about 400° C., a pressure of about 200 kPa to about 20,000 kPa, such as about 500 to about 5000 kPa and a weight hourly space velocity of about 0.1 to about 10,000 hr$^{-1}$, such as about 1 to about 1,000 hr$^{-1}$. $CO_2$ conversion levels are typically between 20 and 100% and preferably greater than 90%, such as greater than 99%. This exothermic reaction may be carried out in multiple catalyst beds with heat removal between beds. In addition, the lead bed(s) may be operated at higher temperatures to maximize kinetic rates and the tail beds(s) may be operated at lower temperatures to maximize thermodynamic conversion.

The main products of the reaction are water and, depending on the $H_2$:$CO_2$ molar ratio, methane, ethane and higher alkanes, together with some unsaturated $C_2$ and higher hydrocarbons. In addition, some partial hydrogenation of the carbon dioxide to carbon monoxide is preferred. After removal of the water, the methane, carbon monoxide, any unreacted carbon dioxide and higher hydrocarbons can be fed directly to the dehydrocyclization step to generate additional aromatic products.

Fischer-Tropsch Process

In another embodiment the hydrogen rejection step comprises reaction of at least part of the hydrogen in the dehydrocyclization effluent with carbon monoxide according to the Fischer-Tropsch process to produce $C_2$ to $C_5$ paraffins and olefins.

The Fischer-Tropsch process is well known in the art, see for example, U.S. Pat. Nos. 5,348,982 and 5,545,674 incorporated herein by reference. The process typically involves the reaction of hydrogen and carbon monoxide in a molar ratio of about 0.5:1 to about 4:1, preferably about 1.5:1 to about 2.5:1, at a temperature of about 175° C. to about 400° C., preferably about 180° C. to about 240° C. and a pressure of about 1 to about 100 bar (100 to 10,000 kPa), preferably about 10 to about 40 bar (1,000 to 4,000 kPa), in the presence of a Fischer-Tropsch catalyst, generally a supported or unsupported Group VIII, non-noble metal, e.g., Fe, Ni, Ru, Co, with or without a promoter, e.g. ruthenium, rhenium, hafnium, zirconium, titanium. Supports, when used, can be refractory metal oxides such as Group IVB, i.e., titania, zirconia, or silica, alumina, or silica-alumina. In one embodiment, the catalyst comprises a non-shifting catalyst, e.g., cobalt or ruthenium, preferably cobalt, with rhenium or zirconium as a promoter, preferably cobalt and rhenium supported on silica or titania, preferably titania.

In another embodiment, the hydrocarbon synthesis catalyst comprises a metal, such as Cu, Cu/Zn or Cr/Zn, on the ZSM-5 and the process is operated to generate significant quantities of single-ring aromatic hydrocarbons. An example of such a process is described in *Study of Physical Mixtures of $Cr_2O_3$-ZnO and ZSM-5 Catalysts for the Transformation of Syngas into Liquid Hydrocarbons* by Jose Erena; Ind. Eng. Chem. Res. 1998, 37, 1211-1219, incorporated herein by reference.

The Fischer-Tropsch liquids, i.e., $C_5$+, are recovered and light gases, e.g., unreacted hydrogen and CO, $C_1$ to $C_3$ or $C_4$ and water are separated from the heavier hydrocarbons. The heavier hydrocarbons can then be recovered as products or fed to the dehydrocyclization step to generate additional aromatic products.

The carbon monoxide required for the Fischer-Tropsch reaction can be provided wholly or partly by the carbon monoxide present in or cofed with the methane-containing feed and generated as a by-product in the dehydrocyclization step. If required, additional carbon monoxide can be generated by feeding carbon dioxide contained, for example, in natural gas, to a shift catalyst whereby carbon monoxide is produced by the reverse water gas shift reaction:

$$CO_2 + H_2 \leftrightarrow CO + H_2O \qquad \text{(Reaction 8)}$$

and by the following reaction:

$$CH_4 + H_2O \leftrightarrow CO + 3H_2$$

Alcohol Synthesis

In a further embodiment the hydrogen rejection step comprises reaction of at least part of the hydrogen in the dehydrocyclization effluent with carbon monoxide to produce $C_1$ to $C_3$ alcohols, and particularly methanol. The production of methanol and other oxygenates from synthesis gas is also well-known and is described in, for example, in U.S. Pat. Nos. 6,114,279; 6,054,497; 5,767,039; 5,045,520; 5,254,520; 5,610,202; 4,666,945; 4,455,394; 4,565,803; 5,385,949, the descriptions of which are incorporated herein by reference. Typically, the synthesis gas employed has a molar ratio of hydrogen ($H_2$) to carbon oxides ($CO+CO_2$) in the range of from about 0.5:1 to about 20:1, preferably in the range of from about 2:1 to about 10:1, with carbon dioxide optionally being present in an amount of not greater than 50% by weight, based on total weight of the syngas.

The catalyst used in the methanol synthesis process generally includes an oxide of at least one element selected from the group consisting of copper, silver, zinc, boron, magnesium, aluminum, vanadium, chromium, manganese, gallium, palladium, osmium and zirconium. Conveniently, the catalyst is a copper based catalyst, such as in the form of copper oxide, optionally in the presence of an oxide of at least one element selected from silver, zinc, boron, magnesium, aluminum, vanadium, chromium, manganese, gallium, palladium, osmium and zirconium. Conveniently, the catalyst contains copper oxide and an oxide of at least one element selected from zinc, magnesium, aluminum, chromium, and zirconium. In one embodiment, the methanol synthesis catalyst is selected from the group consisting of: copper oxides, zinc oxides and aluminum oxides. More preferably, the catalyst contains oxides of copper and zinc.

The methanol synthesis process can be conducted over a wide range of temperatures and pressures. Suitable temperatures are in the range of from about 150° C. to about 450° C., such as from about 175° C. to about 350° C., for example from about 200° C. to about 300° C. Suitable pressures are in the range of from about 1,500 kPa to about 12,500 kPa, such as from about 2,000 kPa to about 10,000 kPa, for example 2,500 kPa to about 7,500 kPa. Gas hourly space velocities vary depending upon the type of process that is used, but generally the gas hourly space velocity of flow of gas through the catalyst bed is in the range of from about 50 $hr^{-1}$ to about 50,000 $hr^{-1}$, such as from about 250 $hr^{-1}$ to about 25,000 $hr^{-1}$, more preferably from about 500 $hr^{-1}$ to about 10,000 $hr^{-1}$. This exothermic reaction may be carried out in either fixed or fluidized beds, including multiple catalyst beds with heat removal between beds. In addition, the lead bed(s) may be operated at higher temperatures to maximize kinetic rates and the tail beds(s) may be operated at lower temperatures to maximize thermodynamic conversion.

The resultant methanol and/or other oxygenates can be sold as a separate product, can be used to alkylate the aromatics generated in the dehydrocyclization step to higher value products, such as xylenes, or can be used as a feedstock for the production of lower olefins, particularly ethylene and propylene. The conversion of methanol to olefins is a well-known process and is, for example, described in U.S. Pat. No. 4,499,327, incorporated herein by reference.

Selective Hydrogen Combustion

In yet another embodiment, the hydrogen rejection step comprises selective hydrogen combustion, which is a process in which hydrogen in a mixed stream is reacted with oxygen to form water or steam without substantially reacting hydrocarbons in the stream with oxygen to form carbon monoxide, carbon dioxide, and/or oxygenated hydrocarbons. Generally, selective hydrogen combustion is carried out in the presence of an oxygen-containing solid material, such as a mixed metal oxide, that will release a portion of the bound oxygen to the hydrogen.

One suitable selective hydrogen combustion process is described in U.S. Pat. No. 5,430,210, incorporated herein by reference, and comprises contacting at reactive conditions a first stream comprising hydrocarbon and hydrogen and a second stream comprising oxygen with separate surfaces of a membrane impervious to non-oxygen containing gases, wherein said membrane comprises a metal oxide selective for hydrogen combustion, and recovering selective hydrogen combustion product. The metal oxide is typically a mixed metal oxide of bismuth, indium, antimony, thallium and/or zinc.

U.S. Pat. No. 5,527,979, incorporated herein by reference, describes a process for the net catalytic oxidative dehydrogenation of alkanes to produce alkenes. The process involves simultaneous equilibrium dehydrogenation of alkanes to alkenes and the selective combustion of the hydrogen formed to drive the equilibrium dehydrogenation reaction further to the product alkenes. In particular, the alkane feed is dehydrogenated over an equilibrium dehydrogenation catalyst in a first reactor, and the effluent from the first reactor, along with oxygen, is then passed into a second reactor containing a metal oxide catalyst which serves to selectively catalyze the combustion of hydrogen. The equilibrium dehydrogenation catalyst may comprise platinum and the selective metal oxide combustion catalyst may contain bismuth, antimony, indium, zinc, thallium, lead and tellurium or a mixture thereof.

U.S. Patent Application Publication No. 2004/0152586, published Aug. 5, 2004 and incorporated herein by reference, describes a process for reducing the hydrogen content of the effluent from a cracking reactor. The process employs a catalyst system comprising (1) at least one solid acid cracking component and (2) at least one metal-based selective hydrogen combustion component consisting essentially of (a) a metal combination selected from the group consisting of:

i) at least one metal from Group 3 and at least one metal from Groups 4-15 of the Periodic Table of the Elements;
  ii) at least one metal from Groups 5-15 of the Periodic Table of the Elements, and at least one metal from at least one of Groups 1, 2, and 4 of the Periodic Table of the Elements;
  iii) at least one metal from Groups 1-2, at least one metal from Group 3, and at least one metal from Groups 4-15 of the Periodic Table of the Elements; and
  iv) two or more metals from Groups 4-15 of the Periodic Table of the Elements and (b) at least one of oxygen and sulfur, wherein the at least one of oxygen and sulfur is chemically bound both within and between the metals.

The selective hydrogen combustion reaction of the present invention is generally conducted at a temperature in the range of from about 300° C. to about 850° C. and a pressure in the range of from about 1 atm to about 20 atm (100 to 2000 kPa).

Aromatic Product Recovery/Treatment

The major products of the dehydrocyclization step are benzene and naphthalene. These products can be separated from the dehydrocyclization effluent, typically by solvent extraction followed by fractionation, and then sold directly as commodity chemicals. Alternatively, some or all of the benzene and/or naphthalene can be alkylated to produce, for example, toluene, xylenes and alkyl naphthalenes and/or can be subjected to hydrogenation to produce, for example, cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). Suitable alkylation and hydrogenation processes are described below and in more detail in our copending PCT Application Nos. PCT/US2005/043523, filed on Dec. 2, 2005 and PCT/US2005/044038, filed on Dec. 2, 2005.

Aromatics Alkylation

Alkylation of aromatic compounds such as benzene and naphthalene is well known in the art and typically involves reaction of an olefin, alcohol or alkyl halide with the aromatic species in the gas or liquid phase in the presence of an acid catalyst. Suitable acid catalysts include medium pore zeolites (i.e., those having a Constraint Index of 2-12 as defined in U.S. Pat. No. 4,016,218), including materials having the framework types MFI (e.g., ZSM-5 and silicalite), MEL (e.g., ZSM-11), MTW (e.g., ZSM-12), TON (e.g., ZSM-22), MTT (e.g., ZSM-23), MFS (e.g., ZSM-57) and FER (e.g., ZSM-35) and ZSM-48, as well as large pore zeolites (i.e, those having a Constraint Index of less than 2) such as materials having the framework types BEA (e.g., zeolite beta), FAU (e.g., ZSM-3, ZSM-20, zeolites X, Y, ultrastabilized Y and dealuminized Y), MOR (e.g., mordenite), MAZ (e.g., ZSM-4), MEI (e.g., ZSM-18) and MWW (e.g., MCM-22, PSH-3, SSZ-25, ERB-1, ITQ-1, ITQ-2, MCM-36, MCM-49 and MCM-56).

In one embodiment of the present process, benzene is recovered from the dehydrocyclization effluent and then alkylated with an olefin, such as ethylene produced as a by-product of a hydrogen rejection step employing ethanation/methanation. Typical conditions for carrying out the vapor phase alkylation of benzene with ethylene include a temperature of from about 650 to 900° F. (343 to 482° C.), a pressure of about atmospheric to about 3000 psig (100 to 20,800 kPa), a WHSV based on ethylene of from about 0.5 to about 2.0 hr$^{-1}$ and a mole ratio of benzene to ethylene of from 1:1 to 30:1. Liquid phase alkylation of benzene with ethylene may be carried out at a temperature between 300 and 650° F. (150 to 340° C.), a pressure up to about 3000 psig (20,800 kPa), a WHSV based on ethylene of from about 0.1 to about 20 hr$^{-1}$ and a mole ratio of benzene to ethylene of from 1:1 to 30:1.

Preferably, the benzene ethylation is conducted under at least partial liquid phase conditions using a catalyst comprising at least one of zeolite beta, zeolite Y, MCM-22, PSH-3, SSZ-25, ERB-1, ITQ-1, ITQ-2, ITQ-13, ZSM-5 MCM-36, MCM-49 and MCM-56.

The benzene ethylation can be conducted at the site of the dehydrocyclization/hydrogen rejection process or the benzene can be shipped to another location for conversion to ethylbenzene. The resultant ethylbenzene can then be sold, used as a precursor in, for example, the production of styrene or isomerized by methods well known in the art to mixed xylenes.

In another embodiment of the present process, the alkylating agent is methanol or dimethylether (DME) and is used to alkylate benzene and/or naphthalene recovered from the dehydrocyclization effluent to produce toluene, xylenes, methylnaphthalenes and/or dimethylnaphthalenes. Where the methanol or DME is used to alkylate benzene, this is conveniently effected in presence of catalyst comprising a zeolite, such as ZSM-5, zeolite beta, ITQ-13, MCM-22, MCM-49, ZSM-11, ZSM-12, ZSM-22, ZSM-23, ZSM-35, and ZSM-48, which has been modified by steaming so as to have a Diffusion Parameter for 2,2 dimethylbutane of about 0.1-15 sec$^{-1}$ when measured at a temperature of 120° C. and a 2,2 dimethylbutane pressure of 60 torr (8 kPa). Such a process is selective to the production of para-xylene and is described in, for example, U.S. Pat. No. 6,504,272, incorporated herein by reference. Where the methanol is used to alkylate naphthalene, this is conveniently effected in the presence of a catalyst comprising ZSM-5, MCM-22, PSH-3, SSZ-25, ERB-1, ITQ-1, ITQ-2, ITQ-13, MCM-36, MCM-49 or MCM-56. Such a process can be used to selectively produce 2,6-dimethylnaphthalene and is described in, for example, U.S. Pat. Nos. 4,795,847 and 5,001,295, incorporated herein by reference.

Where methanol or DME is used as an alkylating agent in the process of the invention, it can be provided as a separate feed to the process or can at least partly be generated in situ by adding a carbon dioxide-containing feed gas, such as a natural gas stream, to part or all of the effluent from the dehydrocyclization step. In particular, the dehydrocyclization effluent, prior to any separation of the aromatic components, can be fed to a reverse shift reactor and reacted with the carbon dioxide-containing feed under conditions to increase the carbon monoxide content of the effluent by reactions, such as Reactions 5 and 8 above.

In addition, methane and $CO_2$ and/or steam may be fed to a reverse shift reactor to generate syngas which can then be mixed with a portion of the dehydrocyclization effluent to adjust the $H_2/CO/CO_2$ ratios as required for the alkylation step.

Typically, the reverse shift reactor contains a catalyst comprising a transition metal on a support, such as Fe, Ni, Cr, Zn on alumina, silica or titania, and is operated under conditions including a temperature of about 500° C. to about 1200° C., such as about 600° C. to about 1000° C., for example about 700° C. to about 950° C. and a pressure of about 1 kPa to about 10,000 kPa, such as about 2,000 kPa to about 10,000 kPa, for example about 3000 kPa to about 5,000 kPa. Gas hourly space velocities may vary depending upon the type of process used, but generally the gas hourly space velocity of flow of gas through the catalyst bed is in the range of about 50 hr$^{-1}$ to about 50,000 hr$^{-1}$, such as about 250 hr$^{-1}$ to about 25,000 hr$^{-1}$, more preferably about 500 hr$^{-1}$ to about 10,000 hr$^{-1}$.

The effluent from the reverse shift reactor can then be fed to an alkylation reactor operating under conditions to cause reactions such as the following to occur:

$$CO + 2H_2 \leftrightarrow CH_3OH \qquad \text{(Reaction 9)}$$

$$CH_3OH + C_6H_6 \rightarrow \text{toluene} + 2H_2O \qquad \text{(Reaction 10)}$$

$$2CH_3OH + C_6H_6 \rightarrow \text{xylenes} + 2H_2O \qquad \text{(Reaction 11)}$$

Suitable conditions for such an alkylation reactor would include a temperature of about 100 to about 700° C., a pressure of about 1 to about 300 atmospheres (100 to 30,000 kPa), and a WHSV for the aromatic hydrocarbon of about 0.01 to about 100 hr$^{-1}$. A suitable catalyst would comprise a molecular sieve having a constraint index of 1 to 12, such as ZSM-5, typically together with one or metals or metal oxides, such as copper, chromium and/or zinc oxide.

Preferably, where the alkylation catalyst includes a molecular sieve, the latter is modified to change its diffusion characteristics such that the predominant xylene isomer produced by Reaction 11 is paraxylene. Suitable means of diffusion modification include steaming and ex-situ or in-situ deposition of silicon compounds, coke, metal oxides, such as MgO, and/or P on the surface or in the pore mouths of the molecular sieve. Also preferred is that an active metal incorporated into the molecular sieve so as to saturate more highly reactive species, such as olefins, which may be generated as by-products and which could otherwise cause catalyst deactivation.

The effluent from the alkylation reactor could then be fed to a separation section in which the aromatic products would initially be separated from the hydrogen and other low molecular weight materials, conveniently by solvent extraction. The aromatics products could then be fractionated into a benzene fraction, a toluene fraction, a $C_8$ fraction and a heavy fraction containing naphthalene and alkylated naphthalenes. The $C_8$ aromatic fraction could then be fed to a crystallization or sorption process to separate the valuable p-xylene component and the remaining mixed xylenes either sold as product or fed to an isomerization loop to generate more p-xylene. The toluene fraction could either be removed as saleable product, recycled to the alkylation reactor or fed to a toluene disproportionation unit, and preferably a selective toluene disproportionation unit for the preparation of additional p-xylene.

Aromatics Hydrogenation

In addition to or instead of the alkylation step, at least part of the aromatic components in the dehydrocyclization effluent can be hydrogenated to generate useful products such as cyclohexane, cyclohexene, dihydronaphthalene (benzylcyclohexene), tetrahydronaphthalene (tetralin), hexahydronaphthalene (dicyclohexene), octahydronaphthalene and/or decahydronaphthalene (decalin). These products can be employed as fuels and chemical intermediates and, in the case of tetralin and decalin, can be used as the solvent for extracting the aromatic components from the dehydrocyclization effluent.

The hydrogenation is conveniently, but not necessarily, conducted after separation of the aromatic components from the dehydrocyclization effluent and conveniently employs part of the hydrogen generated by the dehydrocyclization reaction. Suitable aromatic hydrogenation processes are well known in the art and typically employ a catalyst comprising Ni, Pd, Pt, Ni/Mo or sulfided Ni/Mo supported on alumina or silica support. Suitable operating conditions for the hydrogenation process include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 hr$^{-1}$, such as about 2 to about 10 hr$^{-1}$.

Partial hydrogenation to leave one or more olefinic carbon-carbon bonds in the product may also be desirable so as to produce materials suitable for polymerization or other downstream chemical conversion. Suitable partial hydrogenation processes are well known in the art and typically employ a catalyst comprising noble metals with ruthenium being preferred supported on metallic oxides, such as $La_2O_3$—ZnO. Homogeneous noble metal catalyst systems can also be used. Examples of partial hydrogenation processes are disclosed in U.S. Pat. Nos. 4,678,861; 4,734,536; 5,457,251; 5,656,761; 5,969,202; and 5,973,218, the entire contents of which are incorporated herein by reference.

An alternative hydrogenation process involves low pressure hydrocracking of the naphthalene component to produce alkylbenzenes over a catalyst such as sulfided Ni/W or sulfided Ni supported on an amorphous aluminosilicate or a zeolite, such as zeolite X, zeolite Y or zeolite beta. Suitable operating conditions for low pressure hydrocracking include a temperature of about 300 to about 1,000° F. (150 to 540° C.), such as about 500 to about 700° F. (260 to 370° C.), a pressure of about 50 to about 2,000 psig (445 to 13890 kPa), such as about 100 to about 500 psig (790 to 3550 kPa) and a WHSV of about 0.5 to about 50 hr$^{-1}$, such as about 2 to about 10 hr$^{-1}$.

Various non-limiting embodiments of the invention will now be more particularly described with reference to the accompanying drawings and the Examples.

FIG. 1 illustrates a simplified design of a dehydrocyclization reactor and a catalyst reheater according to a first embodiment of the invention. In this embodiment, the dehydrocyclization reactor includes a vertically disposed settling bed reactor 11, into which heated catalyst flows through an inlet 12 located adjacent the top of the reactor 11 and from which cooled catalyst flows by way of a valved outlet 13 located adjacent the base of the reactor 11. Typically, the heated catalyst enters the reactor 11 at a temperature of about 900° C. and the cooled catalyst leaves the reactor at a temperature of about 650° C.

Methane feedstock 14 is introduced into the reactor 11 adjacent the base of the reactor and additional methane or methane plus air 15 as supplemental fuel is used to transport the cooled catalyst to a catalyst reheater 16. Typically, the amount of methane used as the supplemental fuel is about 120 wt % of the amount of methane used as the feed 14 to the dehydrocyclization process when the objective is to co-produce synthesis gas. Typically the amount of methane used as supplemental fuel is about 65 wt % of the amount of methane used as the feed 14 to the dehydrocyclization process when the objective is not to co-produce synthesis gas.

The catalyst reheater 16 is in the form of a vertically disposed riser, with the cooled catalyst being transported up through the riser by the methane fuel and with oxygen being injected into the riser through a plurality of inlets 17 spaced along the length of the riser. The oxygen injected into the reheater 16 causes the methane fuel to burn and thereby raises the temperature of the catalyst as it flows through the riser. The amount of oxygen introduced through each inlet 17 is controlled so as to maintain an oxygen-lean atmosphere in the riser, whereby burning of the supplemental fuel and hence heating of the catalyst occurs gradually as the catalyst flows up through the riser. This minimizes exposure of the catalyst to excessively high temperatures and also results in incomplete oxidation of the fuel such that the combustion effluent is rich in carbon monoxide. The combustion effluent exits the reactor 16 through an outlet 18 and typically comprises 59 wt % $H_2$, 30 wt % CO, 8 wt % $H_2O$ and 3 wt % $CO_2$. Thus the combustion effluent comprises a convenient source of synthesis gas which can be used to generate additional hydrocarbon product and/or fuel.

At or adjacent the top of the riser 16, the heated catalyst passes into a catalyst stripper 19, where the catalyst is contacted with additional methane to remove water or oxygen that may have been adsorbed by the catalyst, before the heated catalyst is returned to the reactor 11 through the inlet 12. Process effluent, containing aromatic hydrocarbons, is removed from the reactor 11 by way of an outlet (not shown) at or near the top of the reactor 11.

Figure 2:
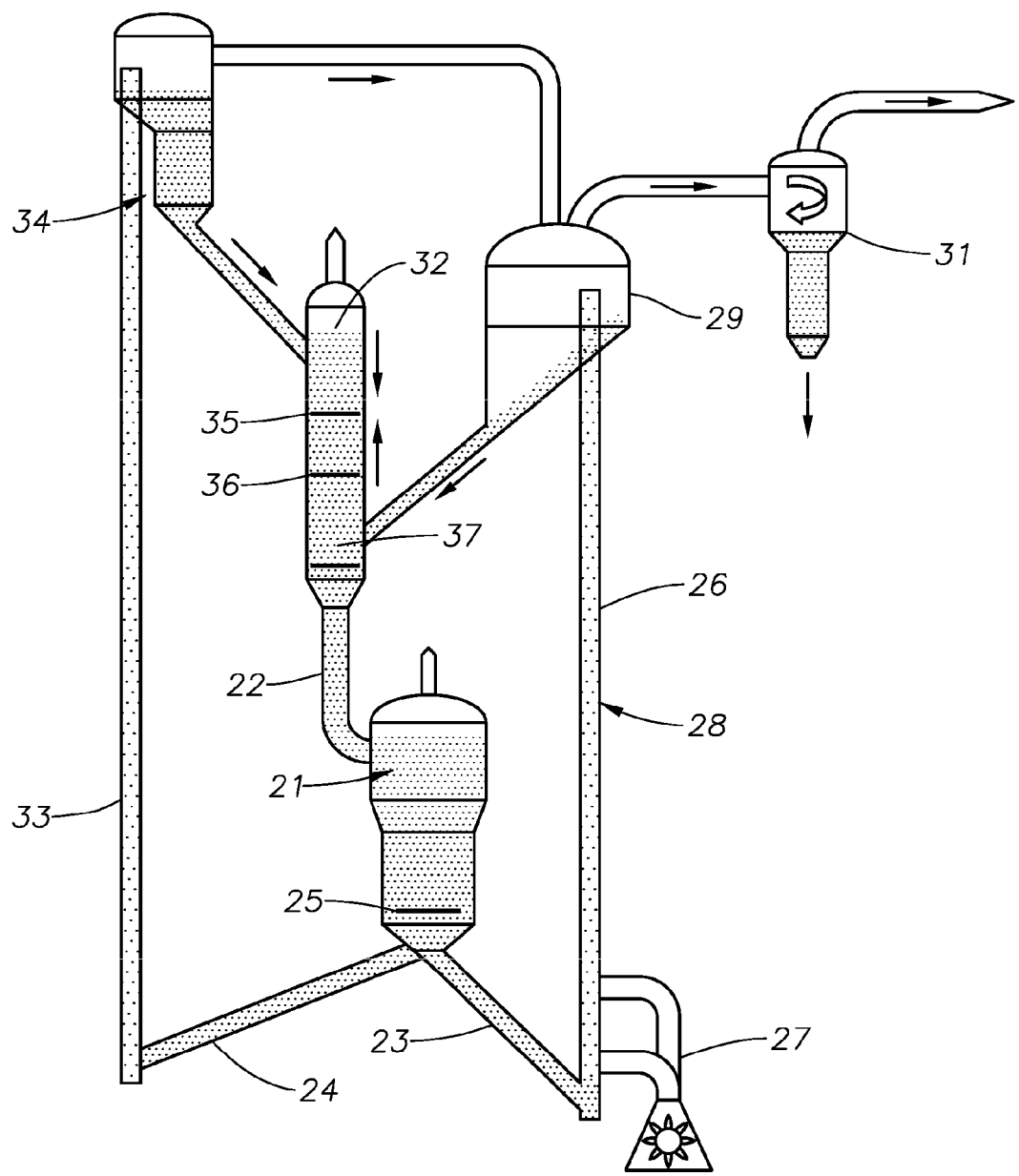
FIG. 2 is a diagram of a dehydrocyclization reactor with a catalyst reheater and a catalyst regenerator according to a second embodiment of the invention.

A second embodiment of the invention is shown in FIG. 2, in which a dehydrocyclization reactor is provided with both a catalyst reheater and a separate catalyst regenerator. As in the first example, the dehydrocyclization reactor includes a vertically disposed settling bed reactor 21, into which heated catalyst flows through an inlet 22 located adjacent the top of the reactor 21 and from which cooled catalyst flows by way of first and second outlets 23, 24 respectively located adjacent the base of the reactor 21. Methane feed 25 is introduced into the reactor 21 adjacent the base thereof.

A first portion of the cooled catalyst flows under gravity from the first outlet 23 to the base of a riser reheater 26, where the catalyst is entrained in a mixture of air and methane fuel passed into the riser through a manifold 27. The catalyst is transported up the riser 26 by the air/methane mixture and is heated during its passage through the riser 26 by combustion of the methane. The mixture entering the riser 26 through the manifold 27 contains all the fuel required to heat the catalyst to the required reaction temperature, but is deficient in oxygen. Additional air is therefore introduced into the riser 26 through a plurality of inlets 28 spaced along the length of the riser (for simplicity only two inlets 28 are indicated in FIG. 2 but in reality the number may be far greater), whereby heating of the catalyst occurs gradually as the catalyst flows up through the riser 26.

On exiting the top of the riser 26, the heated catalyst passes into a separator 29 where the solid particulate catalyst is separated from the combustion gases and then passed to an activator/stripper tower 32. The combustion gases are then fed to cyclones 31 for removal of catalyst fines before being subjected to heat recovery. Using air as the combustion medium in the reheater, the combustion gases typically comprise 67.9 wt % $N_2$, 0.2 wt % $O_2$, 1.3 wt % $H_2$, 3.6 wt % CO, 7.9 wt % $CO_2$, and 17.3 wt % $H_2O$.

A second portion of the cooled catalyst flows under gravity from the second outlet 24 to the base of a riser regenerator 33 where the catalyst is entrained in a stream of oxygen-containing gas and transported up the riser regenerator. As the second catalyst portion passes through the regenerator 33 coke generated on the catalyst in the dehydrocyclization reactor 21 is burned off the catalyst thereby heating the catalyst. However, the regenerator 33 is preferably controlled, for example by lowering the temperature of the oxygen-containing gas fed to the regenerator 33, so that the temperature of the second catalyst portion exiting the regenerator is less than the temperature of the second catalyst portion exiting the reactor 21. Typically, the temperature of the second catalyst portion exiting the regenerator 33 is about 550° C. whereas on exiting the reactor 21 the second catalyst portion is at a temperature of about 650° C.

On exiting the top of the regenerator 33, the second catalyst portion passes into a separator 34 where the solid particulate catalyst separates from the combustion gasses, which are then fed to the cyclones 31 for removal of catalyst fines. The separated catalyst particles then flow to the activator/stripper tower 32.

In the activator/stripper tower 32, the regenerated catalyst is initially contacted with a hydrocarbon stream 35, such as methane, ethane or propane as well as $H_2$ and/or CO flowing upwardly from lower parts of the vessel, to recarburize the metal on the catalyst since the regeneration step not only removes surface coke from the catalyst but also tends to oxidize catalytically active carbide species on the metal component of the catalyst. The catalyst is then contacted with a methane stream 36 to remove water or oxygen that may have been adsorbed by the catalyst. The regenerated catalyst is then combined with the reheated catalyst from the riser 26 and the combined catalyst is contacted with a hydrogen and/or $CO_2$ stream 37 remove any residual coke or heavy hydrocarbons. After stripping the catalyst the hot gasses flow upward to help heat the regenerated catalyst portion in the recarburization section. The combined catalyst is then returned to the reactor 21 through the inlet 22. Preferably all the gas streams fed to the vessel are preheated to minimize temperature losses. While the drawing indicates all actions in a single vessel, it is understood that for ease of construction or operation the activities may be carried out in multiple vessels.

Figure 3:
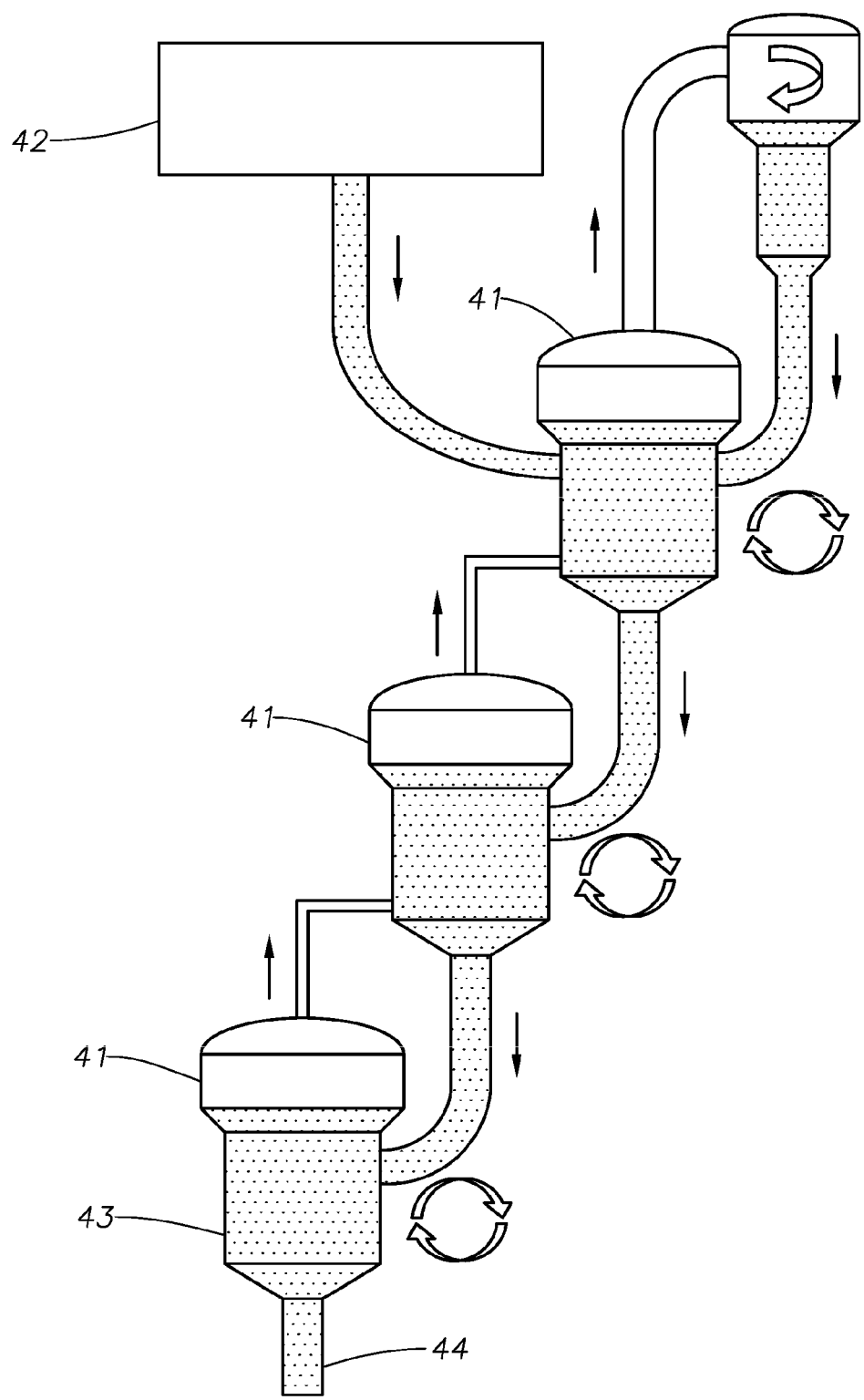
FIG. 3 is a diagram of a multiple fluid bed dehydrocyclization reactor according to a third embodiment of the invention.

A third embodiment of the invention is shown in FIG. 3, in which a dehydrocyclization reactor comprises a plurality, in this case 3, of vertically-spaced, series-connected fluid bed reactors 41 in which hot catalyst from the stripper 42 of a catalyst reheater (not shown) enters the uppermost reactor 41 and moves downwardly in counter-current flow to methane which is introduced through an inlet 43 into the lowermost reactor 41. Cooled catalyst is removed from the lowermost reactor 41 and sent to the catalyst reheater. The reheater and regenerator employed with the fluid bed design of FIG. 3 would typically be the same as those shown in FIG. 2. It will, however, be appreciated that the particle a size of the catalyst employed with the fluid bed design of FIG. 3 would typically be smaller, for example in the range of about 50 μm to about 500 μm, than the particle size of the catalyst employed with the settling bed design of FIGS. 1 and 2, typically in the range of about 1,000 μm to about 10,000 μm.

Figure 4:
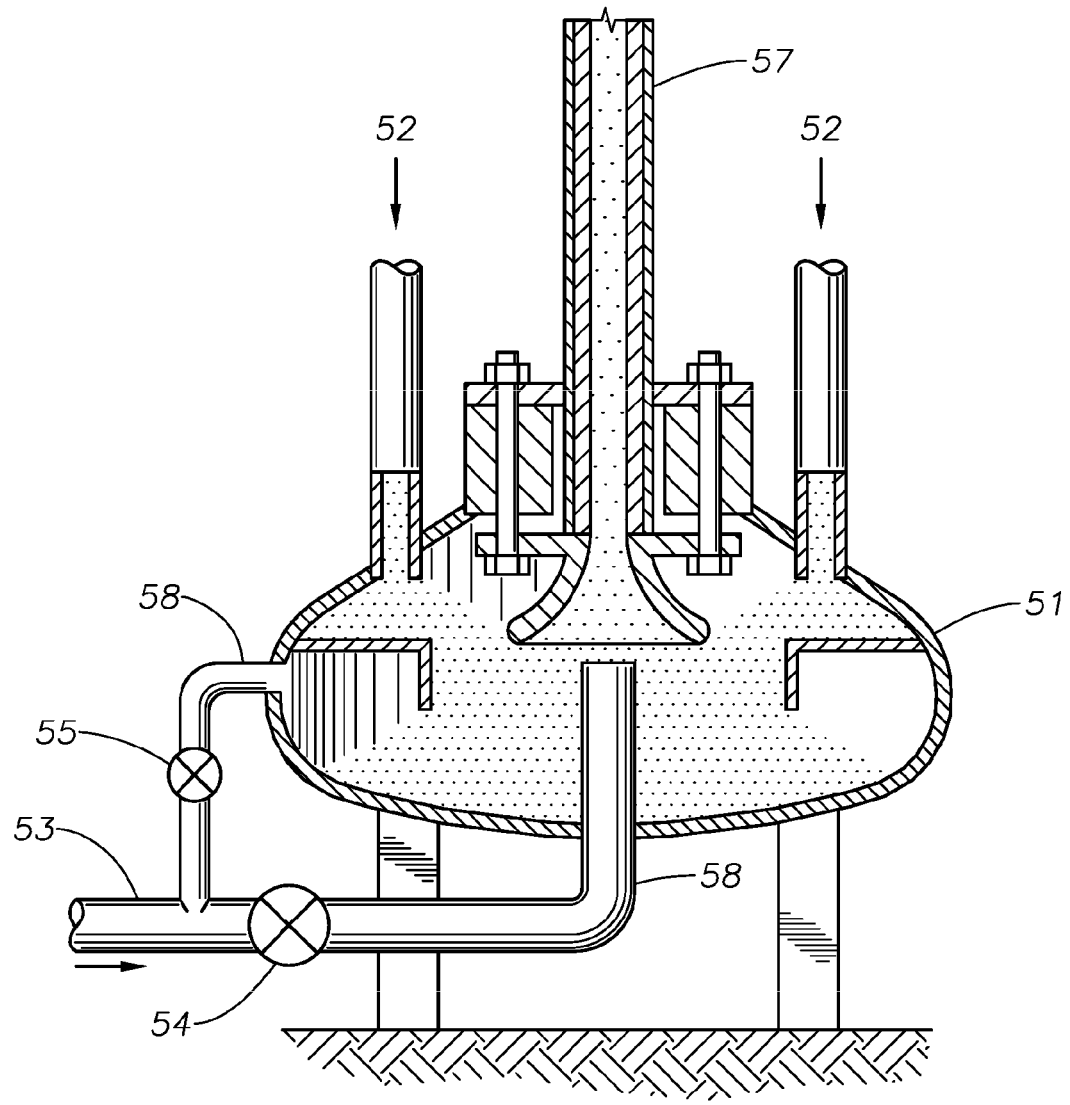
FIG. 4 is a diagram of a catalyst lift apparatus for use with the risers employed in the first, second and third embodiments of the invention.

FIG. 4 illustrates one suitable apparatus for controlling the flow rate of the catalyst through the risers employed in the catalyst reheater of FIGS. 1 and 2 and/or the catalyst regenerator of FIG. 2. The apparatus includes a catalyst collecting tank 51 that accommodates a bed of cooled/spent catalyst received from the dehydrocyclization reactor (not shown) by way of conduits 52. Lift gas either in the form of oxygen-deficient air for regeneration or a fuel/air mixture for catalyst reheating is supplied to tank 51 by way of a conduit 53 and is divided by valves 54, 55 into a primary gas flow and a secondary gas flow. The primary gas flow is fed by a conduit 56 to a region of tank 51 directly below the lower end of a riser 57 such that primary lift gas flows up through the riser 57 without passing through any substantial thickness of the catalyst bed.

The secondary lift gas is fed by a conduit 58 to a region of the tank 51 spaced a substantial distance from the lower end of the riser 57 so that the secondary lift gas has to flow through a substantial thickness of the catalyst bed to reach the riser. The secondary lift gas pushes the catalyst particles into the stream of primary lift gas where they are entrained and lifted up the riser 57. By controlling the valves 54, 55 to vary the relative flow rates of the primary and secondary lift gases, the rate of flow of the catalyst particles through the riser 57, and hence the flow rate of the catalyst within the riser 57, can be varied. Generally, the flow rate of the secondary lift gas is varied between 5 and 15% of the total gas flow.

In the embodiments shown in the drawings the risers employed in the catalyst reheater and the catalyst regenerator have a generally constant internal diameter along the length of the riser. In some case, however, it may be desirable to arrange that the internal diameter of the riser increases from the base to the top of the riser.

Although not shown in the drawings, it is desirable to use "waste heat" from other parts of the process to preheat the methane (both as the feedstock to be converted to aromatics and as the fuel for the catalyst reheater), preferably up to about 600° C. and to preheat the oxygen-containing feed to the catalyst reheater to the maximum available temperature.

EXAMPLE 1

Spatial and Time-Dependence of Catalyst Temperature Profile in Reheater

Internal (spatial) temperature profile within a catalyst particle and its dependence on time axially up the riser was calculated for two cases: (A) when all the air required for methane oxidation is added at riser bottom (i.e., at catalyst residence time in riser of zero), and (B) when the air feed is axially distributed along the riser (either at discrete catalyst residence time intervals as would be practically possible or "continuous" air injection points at infinitesimal time intervals (or riser lengths) to simulate theoretical, best-case performance). The methodology for calculating the time-dependent, temperature profile within the catalyst particle (assumed to be a sphere) T(r, t) involved numerically solving the simplified heat transfer equation for unsteady-state, 1-dimensional heat transfer with no homogenous reaction coupled with convective and radiative heat-transfer boundary condition at the particle surface:

$$\frac{\partial T}{\partial t} = D\left(\frac{\partial^2 T}{\partial r^2} + \frac{2}{r}\frac{\partial T}{\partial r}\right)$$

$$-k\frac{\partial T}{\partial r} = h(T_{surface} - T_{flue}) + \sigma\varepsilon(T^4_{surface} T^4_{flue})$$

where r is the radial distance from the sphere center, t is the catalyst residence time in riser, D is the thermal diffusivity, k is the catalyst thermal conductivity, h is the convective heat-transfer coefficient, $T_{surface}$ and $T_{flue}$ are the catalyst surface temperature (at r=R) and the bulk flue gas temperature (at r>>R), respectively, σ is the Stefan-Boltzmann constant, and ε is the catalyst surface emissivity. For simplicity, we have assumed that the catalyst thermal conductivity, thermal diffusivity and surface emissivity remain constant. The convective heat-transfer coefficient was calculated using flue gas properties at riser top and bottom conditions using Geankoplis correlation for isolated sphere in gas flow. Since the difference in heat-transfer coefficients was <20%, an average value was used throughout the riser. The following Table 1 lists the physical constants and catalyst properties used in the model.

TABLE 1

Model Parameters

| | |
|---|---|
| Catalyst Particle Size | 250 or 3650 microns |
| Catalyst Particle Density | 1400 kg/m³ |
| Catalyst Heat Capacity | 1262 J/kg-K |
| Catalyst Thermal Conductivity | 0.4 W/m-K |
| Catalyst Thermal Diffusivity | 2.26 × 10⁻⁷ m²/s |
| Catalyst Surface Emissivity | 0.85 |
| Catalyst Riser Inlet Temperature | 713 C. |
| Catalyst Riser Outlet Temperature | 850 C. |
| Fuel Gas Composition | 9.5% CH₄, 19% O₂, 71.5% N₂ |
| Fuel Gas Inlet Temperature | 300 C. |
| Flue Gas Outlet Temperature | 900 C. |

In addition to heat-transfer calculations, the overall energy balance between catalyst particle and flue gas needs to be satisfied:

$$H_{out} - H_{in} + \Delta H°_{rxn}\xi + Q_{cat} = 0$$

where $H_{out}$ and $H_{in}$ are the flue gas enthalpies at inlet and outlet conditions (for each time increment), $\Delta H°_{rxn}$ is the enthalpy change due to reaction of ξ moles of methane, and $Q_{cat}$ is the heat transferred to the catalyst during the time increment.

The enthalpy of gas mixtures was calculated using:

$$H - H_{298}(kJ/mol) = At + Bt^2/2 + Ct^3/3 + Dt^4/4 - Et + F - H$$

(where t=T(K)/1000)

where A to H are heat capacity constants for a particular species. The energy balance equation allows calculation of the flue gas temperature axially up the riser.

The heat-transfer partial differential equation was numerically solved using explicit, finite-difference method:

$$\frac{\partial c}{\partial \tau} = \frac{1}{R^2}\frac{\partial}{\partial R}\left(R^2\frac{\partial c}{\partial R}\right) \text{ where } c = \frac{T}{T_o}, \tau = \frac{Dt}{a^2}, R = \frac{r}{a}$$

$$c_{i,j+1} = c_{ij} + \frac{\partial \tau}{i(\partial R)^2}\{(i+1)c_{i+1,j} - 2ic_{i,j} + (i-1)c_{i-1,j}\} \quad i \neq 0$$

$$c_{i,j+1} = c_{ij} + \frac{6\partial \tau}{(\partial R)^2}\{c_{1,j} - c_{0,j}\} \quad i = 0$$

$$c_{N,j+1} = c_{Nj} + \frac{\partial \tau}{N(\partial R)^2}\left\{(N+1)\begin{bmatrix}c_{N-1,j}+\\2\alpha\partial R(c^4_{N,j} - c^4_a)+\\2\beta\partial R(c_{N,j} - c_a)\end{bmatrix} - \\ 2Nc_{N,j} + (N-1)c_{N-1,j}\right\}$$

where subscript i is the radial index from 0 to N, subscript j is the time index, subscript α denotes flue gas property, and α and β are dimensionless radiative and convective boundary condition constants, respectively.

Case A: Complete Air Addition at Riser Bottom

Figure 5:
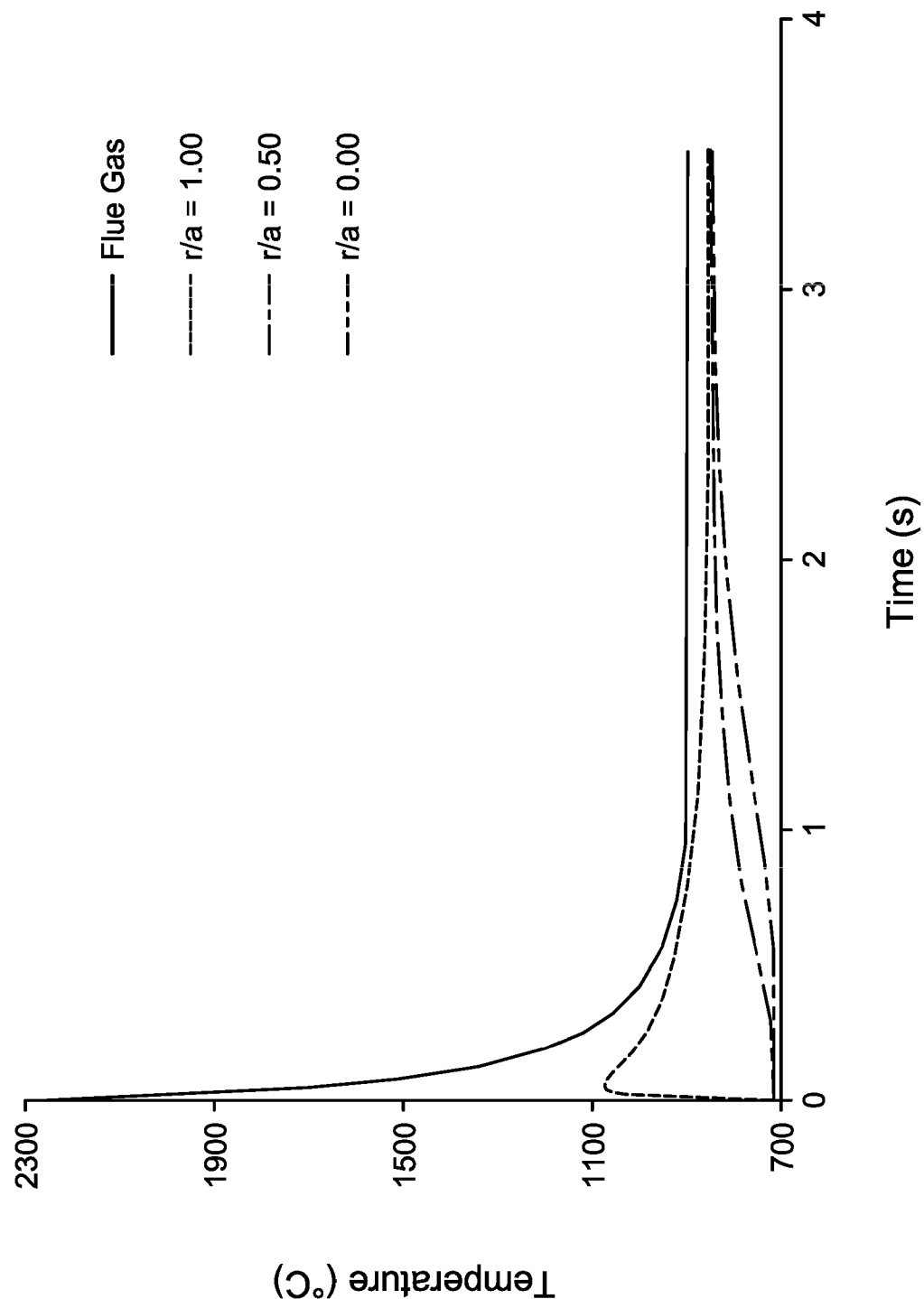
FIG. 5 compares the temperature profile of the flue gas with the temperature profiles at different radial positions within a catalyst particle having a diameter of 3650 μm when heated in a riser with all the heat being supplied by burning fuel at the bottom of the riser.

FIG. 5 shows the catalyst temperature profile for different radial positions within the catalyst particle as a function of catalyst residence time in riser. These profiles were generated for catalyst diameter (α) of 3650 μm, which would be representative for settling-bed (non-fluidized) reactor. The initial flue gas temperature at time of zero is the adiabatic temperature rise of 2254° C. The catalyst particle achieves a mass-average temperature of 850° C. after 0.95 seconds, although substantial internal temperature gradients still exist at this time. After 0.95 seconds, the catalyst particle exits the riser and disengages from the flue gas, followed by equilibration of these internal gradients assuming no further heat-transfer with process gases. After about 3.5 seconds, the catalyst particle reaches equilibrium at 850° C. Due to the initially high flue gas temperatures, the catalyst surface temperature far exceeds the desired 850° C., reaching a maximum of 1073° C. after 0.05 seconds. It should be noted that the time step used in this numerical simulation was 0.0004 seconds in order to accurately capture events at short time scales.

Case B: Axial Distribution of Air Along Riser

Figure 6:
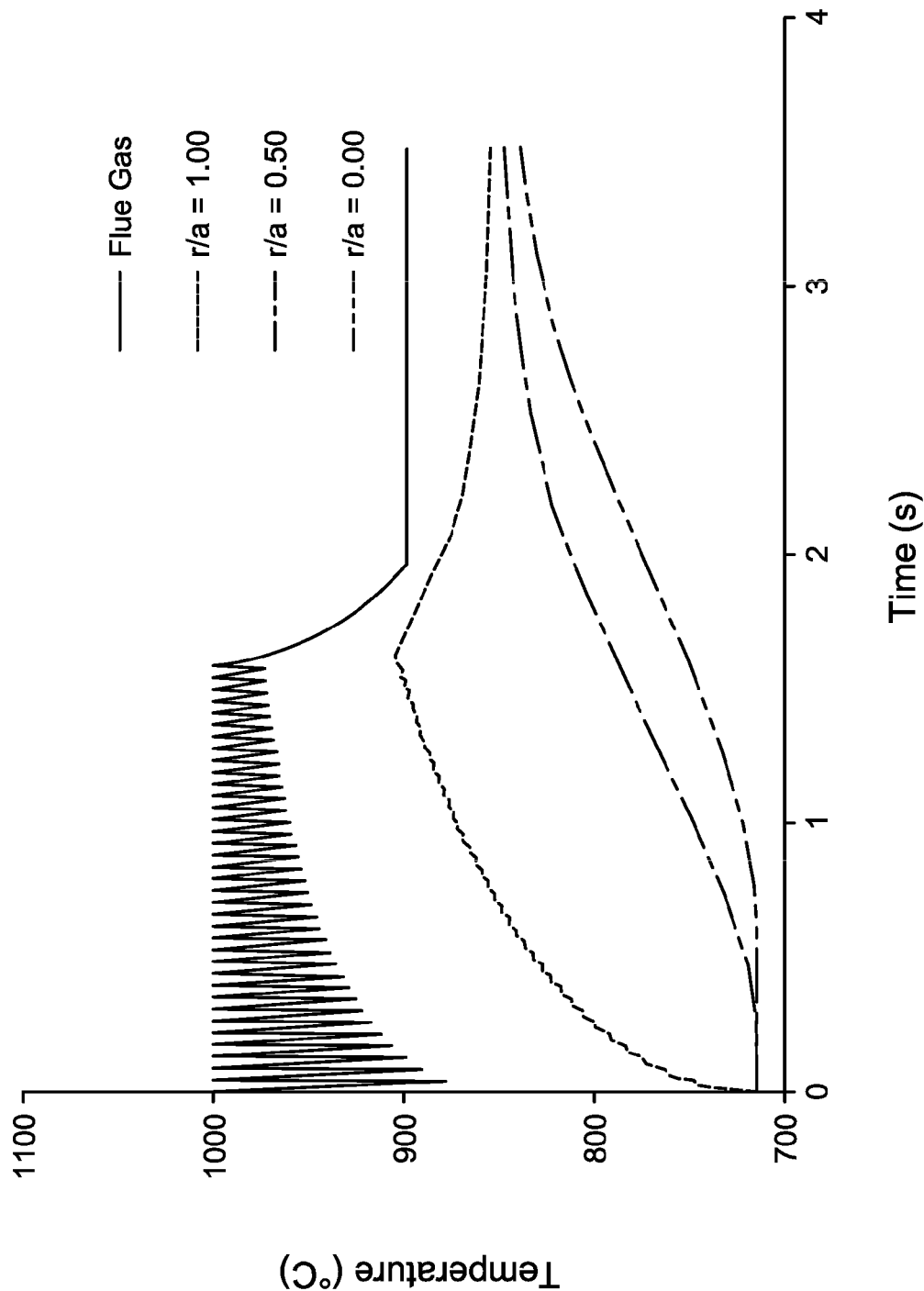
FIG. 6 compares the temperature profile of the flue gas with the temperature profiles at different radial positions within a catalyst particle having a diameter of 3650 μm when heated in a riser with the heat being supplied by burning fuel at spaced positions along the length of the riser.

FIG. 6 shows the catalyst temperature profile for different radial positions within the catalyst particle as a function of catalyst residence time in riser. These profiles were generated for the same catalyst diameter of 3650 μm (as in FIG. 5). Air is distributed along the riser (about 3.5 ft per injection point) and the amount of air added at each injection point is determined by the amount of energy required to raise the flue gas temperature back to 1000° C. After all the available air is utilized, there is no further oxygen injection and the flue gas cools via heat-transfer to solids. The catalyst particle achieves a mass-average temperature of 850° C. after 1.96 seconds, roughly twice the amount of time required for Case A (where all the air was injected at riser bottom), consistent with decreased thermal driving force. However, the maximum surface temperature of 904° C. is substantially lower than 1073° C. for Case A. This approach allows minimizing catalyst exposure to very high temperatures, thereby helping to mitigate catalyst deactivation due to sintering, volatilization or changes in active site, and improve its mechanical integrity due to decreased thermal gradients.

EXAMPLE 2

Control of Maximum Catalyst Surface Temperature

Minimizing catalyst surface temperature is important in limiting hydrothermal deactivation of catalyst in riser. Two factors that can have significant impact on catalyst surface temperature profile are (1) maximum flue gas temperature (manipulated by varying air injection profile along the riser), and (2) catalyst particle size. Other catalyst and fluid properties (such as, thermal conductivity, surface emissivity, convective heat-transfer coefficient, heat capacity etc.) can influence catalyst temperature profiles, but are more difficult to control from a catalyst and/or reactor design perspective. This example demonstrates that by manipulating the flue gas temperature (for a particular catalyst particle size) one can minimize catalyst surface temperatures. In the following simulations, we have used "continuous" air injection points at infinitesimal catalyst residence time intervals (or riser lengths) to maintain a fixed flue gas temperature (until all the air is utilized) to simulate theoretical, best-case performance (i.e., minimum required residence time).

Table 2 shows the simulation results for two particle sizes (1) 3650 μm representative of settling-bed reactor case, and (2) 250 μm representative of fluidized-bed reactor case. For a fixed particle size and choice of initial flue gas temperature, Table 2 shows the maximum surface temperature which a particle would experience during heat-up and the minimum residence time required to raise the average particle temperature to 850° C. For the extreme case when all the air is injected at the riser bottom, the maximum surface temperature for the 250 μm-particles of 871° C. is substantially lower than 1073° C. for 3650 μm-particles, due to their higher surface-to-volume ratio and shorter transport dimension. Moreover, the required residence time is also significantly decreased for smaller particles. At a fixed particle size, lowering the initial flue gas temperature in the isothermal zone decreases the maximum catalyst surface temperature and increases the required residence time. For the extreme case when the flue gas temperature is constant throughout the riser (at 900° C.), the maximum surface temperature for 250 μm-particles is only 5° C. higher than the final average temperature, and 22° C. higher for the 3650 μm-particles. The required residence time for these particle sizes and flue gas temperatures can be achieved using reasonable riser heights and particle velocities.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. In a process for converting methane to higher hydrocarbons including aromatic hydrocarbons, wherein a feed including methane is contacted with a dehydrocyclization catalyst in a reaction zone under conditions effective to convert said methane to aromatic hydrocarbons the improvement comprising a step of heating at least a portion of said catalyst in a heating zone, separate from said reaction zone, with combustion gases generated by burning a supplemental fuel, and then returning the thus-heated catalyst to said reaction zone.

2. The process of claim 1, wherein said combustion gases are generated by burning a hydrocarbon fuel to produce synthesis gas.

3. The process of claim 1, wherein said supplemental fuel is burned in a combustion zone separate from said heating zone and fed to said heating zone.

4. The process of claim 1, wherein said supplemental source of fuel comprises methane.

5. The process of claim 1, wherein said supplemental source of fuel comprises a hydrocarbon and said hydrocarbon is burned in an oxygen-lean atmosphere.

6. The process of claim 1, wherein said at least a portion of said catalyst is at a temperature of 500° C. to 900° C. on entering said heating zone and is at a higher temperature on leaving said heating zone, wherein said higher temperature is between 800° C. and 1000° C.

7. The process of claim 1, further including a step of transferring at least a portion of said catalyst to a regeneration zone, separate from said reaction zone and said heating zone, and contacting said catalyst with a regeneration gas in said regeneration zone to at least partially remove coke deposited on said catalyst in said reaction zone or in said heating zone, whereby said catalyst is at least partially regenerated, and then returning the thus at least partially regenerated catalyst to said reaction zone.

8. The process of claim 7, wherein the temperature in said regeneration zone is less than the temperature in said reaction zone and in the range of 400° C. to 700° C., and wherein said regeneration gas comprises oxygen.

9. The process of claim 7, wherein said regeneration zone is a riser or moving bed reactor, wherein said regeneration gas contains carbon dioxide and/or nitrogen and further contains oxygen, wherein said oxygen is present in the amount of less than 10 wt %, based on the weight of said regeneration gas.

10. The process of claim 7, further comprising a step of contacting the at least partially regenerated catalyst with methane and/or hydrogen to at least partially remove adsorbed water and/or oxygen therefrom before returning said at least partially regenerated catalyst to said reaction zone.

TABLE 2

Dependence of Maximum Catalyst Surface Temperature on Particle Size and Flue Gas Temperature

| Particle Size = 3650 microns | | | Particle Size = 250 microns | | |
|---|---|---|---|---|---|
| Maximum Surface Temperature (C.) | Maximum Flue Gas Temperature (C.) | Minimum Catalyst Residence Time (s) | Maximum Surface Temperature (C.) | Maximum Flue Gas Temperature (C.) | Minimum Catalyst Residence Time (s) |
| 872 | 900 | 3.46 | 855 | 900 | 0.072 |
| 900 | 975 | 1.95 | 871 | 2254 | 0.015 |
| 950 | 1130 | 1.28 | >871 | n/a | n/a |
| 1000 | 1325 | 1.19 | | | |
| 1050 | 1615 | 0.96 | | | |
| 1073 | 2254 | 0.95 | | | |
| >1073 | n/a | n/a | | | |

11. The process of claim 7, wherein said catalyst comprises a metal and wherein said process further includes a carburization step before returning said at least partially regenerated catalyst to said reaction zone.

12. The process of claim 7, wherein said carburization step comprises contacting said regenerated catalyst with at least one gas selected from the group consisting of one or more hydrocarbon, carbon dioxide, and carbon monoxide, optionally in the presence of $H_2$.

\* \* \* \* \*